United States Patent
Goodfried et al.

(10) Patent No.: US 7,799,085 B2
(45) Date of Patent: Sep. 21, 2010

(54) MODULAR IMPLANT SYSTEM WITH FULLY POROUS COATED SLEEVE

(75) Inventors: Gary P. Goodfried, Flint, TX (US); Stephen A. Hazebrouck, Winona Lake, IN (US); Mark B. Lester, Warsaw, IN (US); Scott C. Brown, Warsaw, IN (US)

(73) Assignee: Depuy Products, Inc., Warsaw, IN (US)

( * ) Notice: Subject to any disclaimer, the term of this patent is extended or adjusted under 35 U.S.C. 154(b) by 780 days.

(21) Appl. No.: 10/817,051

(22) Filed: Apr. 2, 2004

(65) Prior Publication Data

US 2005/0107883 A1      May 19, 2005

Related U.S. Application Data

(60) Provisional application No. 60/523,170, filed on Nov. 18, 2003.

(51) Int. Cl.
    *A61F 2/38*      (2006.01)
(52) U.S. Cl. .................................. 623/20.15
(58) Field of Classification Search .............. 623/16.11, 623/18.11, 20.14, 20.15, 20.16, 20.17, 20.19, 623/20.21–20.24, 20.26–20.29, 20.31, 20.35, 623/20.36
    See application file for complete search history.

(56) References Cited

U.S. PATENT DOCUMENTS

| | | | |
|---|---|---|---|
| 3,605,123 A | 9/1971 | Hahn | |
| 3,765,033 A * | 10/1973 | Goldberg et al. | 623/20.26 |
| 3,848,272 A | 11/1974 | Noiles | |
| 3,855,638 A | 12/1974 | Pilliar | |
| 4,219,893 A | 9/1980 | Noiles | |
| 4,301,553 A | 11/1981 | Noiles | |
| 4,536,894 A | 8/1985 | Galante et al. | |
| 4,549,319 A | 10/1985 | Meyer | |
| 4,790,852 A | 12/1988 | Noiles | |
| 4,822,366 A | 4/1989 | Bolesky | |
| 4,822,370 A * | 4/1989 | Schelhas | 623/22.46 |
| 4,846,839 A | 7/1989 | Noiles | |

(Continued)

FOREIGN PATENT DOCUMENTS

EP      1358860 A2      11/2003

OTHER PUBLICATIONS

European Search Report dated Mar. 2, 2005 for European Application No. 04257122.4.

(Continued)

*Primary Examiner*—Anu Ramana

(57) ABSTRACT

A modular knee implant system allows a surgeon to select between several different styles of distal femoral implant components and several different styles of stem extensions while also allowing for use of a metaphyseal component. The metaphyseal component can be a universal one that is usable with all of the styles of distal femoral implant components through use of an adapter. A second adapter allows for use of stem extensions with different types of connectors with the metaphyseal component. A separate metaphyseal component could also be provided with a distal Morse taper post to mate with a distal femoral component having a proximal Morse taper bore. The metaphyseal component may have an outer surface that is configured to maximize contact area with the patient's bone, and may have a surface finish over a substantial part of its overall length that is conducive to bone ingrowth.

11 Claims, 16 Drawing Sheets

U.S. PATENT DOCUMENTS

| | | | |
|---|---|---|---|
| 4,854,496 A | | 8/1989 | Bugle |
| 5,080,685 A | | 1/1992 | Bolesky et al. |
| 5,181,928 A | | 1/1993 | Bolesky et al. |
| 5,286,260 A | | 2/1994 | Bolesky et al. |
| 5,326,359 A | * | 7/1994 | Oudard .................... 623/20.36 |
| 5,330,534 A | | 7/1994 | Herrington et al. |
| 5,344,457 A | * | 9/1994 | Pilliar et al. .................. 606/60 |
| 5,370,706 A | | 12/1994 | Bolesky et al. |
| 5,653,765 A | | 8/1997 | McTighe et al. |
| 5,658,349 A | | 8/1997 | Brooks et al. |
| 5,725,592 A | * | 3/1998 | White et al. ............. 623/23.35 |
| 5,782,921 A | | 7/1998 | Colleran et al. |
| 5,824,097 A | | 10/1998 | Gabriel et al. |
| 5,876,459 A | | 3/1999 | Powell |
| 5,879,391 A | * | 3/1999 | Slamin .................... 623/20.15 |
| 5,906,644 A | | 5/1999 | Powell |
| 6,071,311 A | * | 6/2000 | O'Neil et al. ............ 623/20.15 |
| 6,171,342 B1 | * | 1/2001 | O'Neil et al. ............ 623/20.15 |
| 6,214,052 B1 | | 4/2001 | Burkinshaw |
| 6,264,699 B1 | | 7/2001 | Noiles et al. |
| 6,402,787 B1 | * | 6/2002 | Pope et al. .................. 623/23.6 |
| 6,428,578 B2 | | 8/2002 | White |
| 6,527,807 B1 | | 3/2003 | O'Neil et al. |
| 6,613,092 B1 | | 9/2003 | Kana |
| 6,723,129 B2 | | 4/2004 | Dwyer et al. |
| 6,770,097 B2 | * | 8/2004 | Leclercq .................. 623/20.15 |
| 6,824,566 B2 | | 11/2004 | Kana et al. |
| 6,875,239 B2 | | 4/2005 | Gerbec et al. |
| 6,902,583 B2 | | 6/2005 | Gerbec et al. |

OTHER PUBLICATIONS

Biomet, Orthopaedic Salvage System Overview.
De Puy, Reconstructive/Revision Products, pp. 182 & 184.

\* cited by examiner

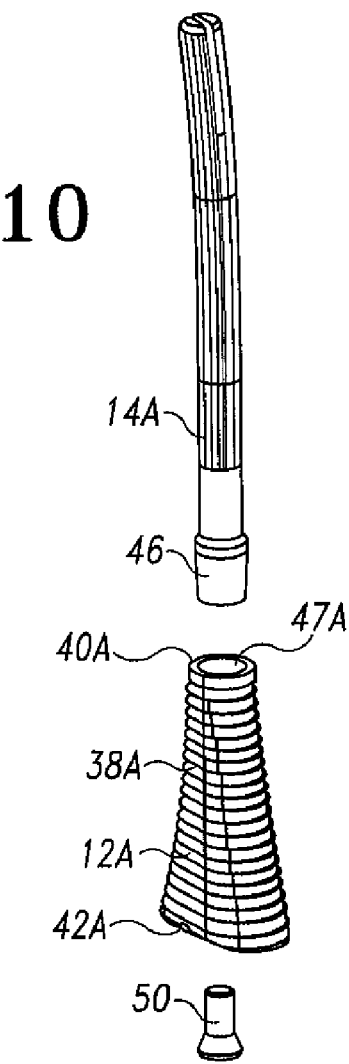
Fig. 10
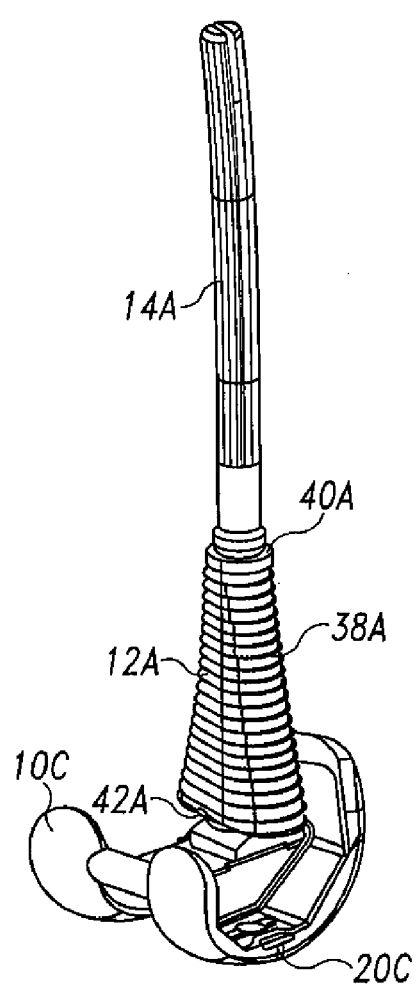
Fig. 9
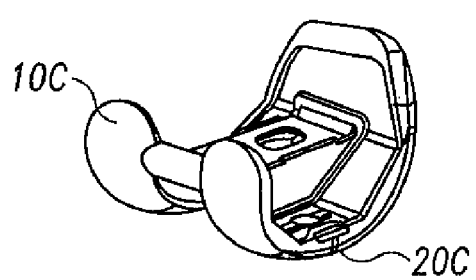

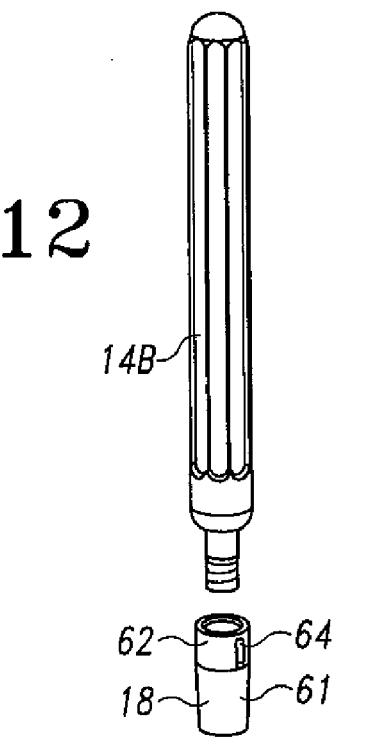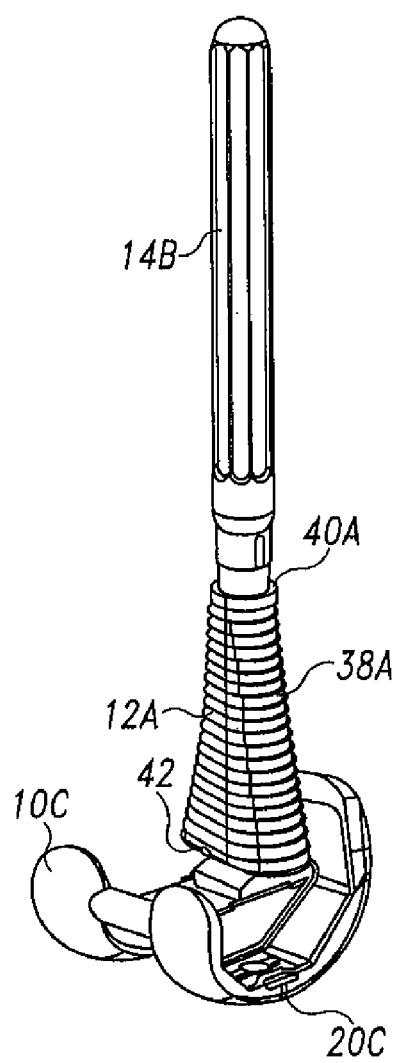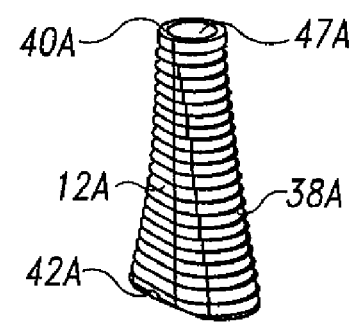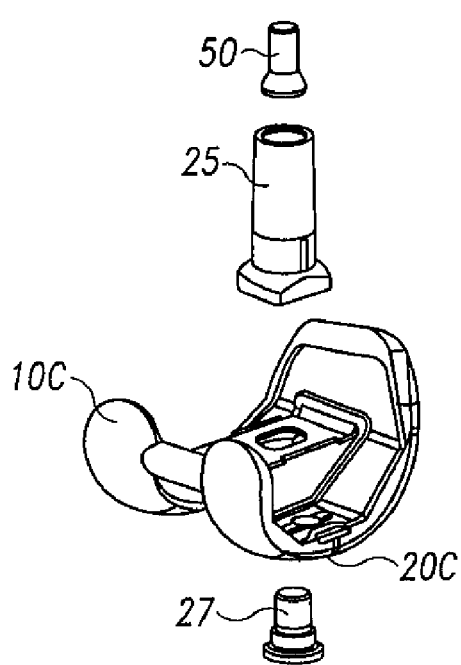
Fig. 12
Fig. 11

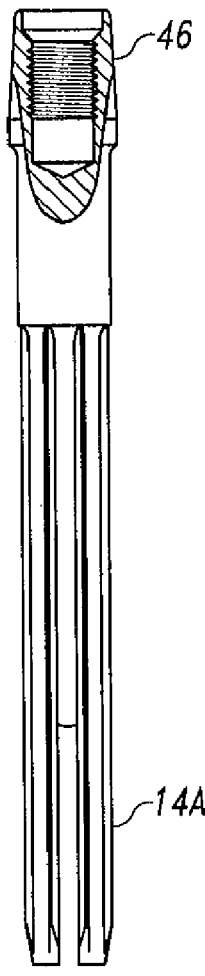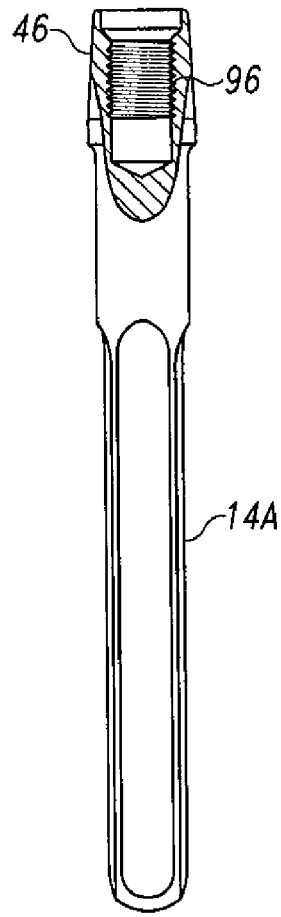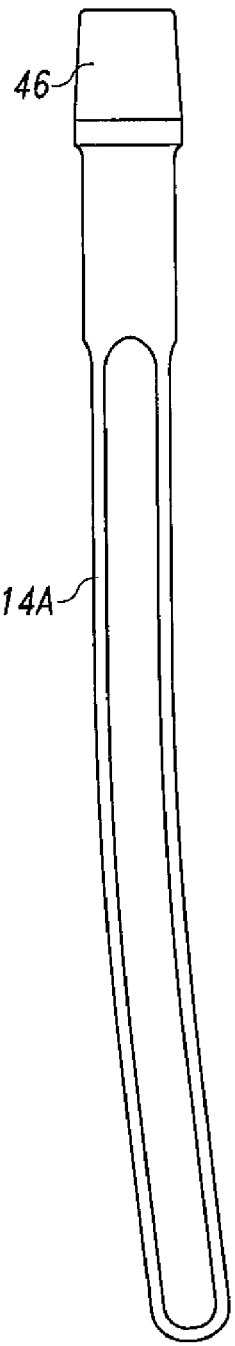
Fig. 37
Fig. 38
Fig. 39

MODULAR IMPLANT SYSTEM WITH FULLY POROUS COATED SLEEVE

This application claims the benefit of U.S. Provisional Application No. 60/523,170 filed on Nov. 18, 2003, which is incorporated by reference herein in its entirety.

BACKGROUND OF THE INVENTION

The present invention relates generally to prosthetic joints and, more particularly, to modular orthopaedic knee implant systems.

The knee joint basically consists of the bone interface of the distal end of the femur and the proximal end of the tibia. Appearing to cover or at least partially protect this interface is the patella which is a sesamoid bone within the tendon of the long muscle (quadriceps) on the front of the thigh. This tendon inserts into the tibial tuberosity and the posterior surface of the patella is smooth and glides over the femur.

The femur is configured with two knob like processes (the medial condyle and the lateral condyle) which are substantially smooth and which articulate with the medial plateau and the lateral plateau of the tibia, respectively. The plateaus of the tibia are substantially smooth and slightly cupped thereby providing a slight receptacle for receipt of the femoral condyles.

When the knee joint is damaged whether as a result of an accident or illness, a prosthetic replacement of the damaged joint may be necessary to relieve pain and to restore normal use to the joint. Typically the entire knee joint is replaced by means of a surgical procedure which involves removal of the surfaces of the corresponding damaged bones and replacement of these surfaces with prosthetic implants. This replacement of a native joint with a prosthetic joint is referred to as a primary total-knee arthroplasty.

On occasion, the primary knee prostheses fails. Failure can result from many causes, including wear, aseptic loosening, osteolysis, ligamentous instability, arthrofibrosis and patellofemoral complications. When the failure is debilitating, revision knee surgery may be necessary. In a revision, the primary knee prosthesis is removed and replaced with components of a revision prosthetic knee system.

Knee implant systems for both primary and revision applications are available from a variety of manufacturers, including DePuy Orthopaedics, Inc. of Warsaw, Ind. DePuy and others offer several different systems for both primary and revision applications. For example, DePuy Orthopaedics offers the P.F.C. SIGMA® Knee System, the LCS® Total Knee System, and the S-ROM Modular Total Knee System. Each of these orthopaedic knee systems includes several components, some appropriate for use in primary knee arthroplasty and some appropriate for use in revision surgery.

DePuy Orthopaedics also offers other orthopaedic implant systems for other applications. One such system is the LPS System. The LPS System is provided for use in cases of severe trauma and disease. In such cases, the trauma or disease can lead to significant amounts of bone loss. The LPS System provides components that can replace all or significant portions of a particular bone, such as the femur. The DePuy LPS System is described more fully in U.S. patent application Ser. No. 10/135,791, entitled "Modular Limb Preservation System", filed Apr. 30, 2002 by Hazebrouck et al., which is incorporated by reference herein in its entirety.

Although each of the implant systems available from DePuy Orthopaedics provides the surgeon with many options in both primary and revision surgery, many of the components of each individual system are generally not interchangeable with the components of the other systems. This lack of interchangeability of system components is also present in implant systems available from other suppliers of orthopaedic implant systems.

SUMMARY OF THE INVENTION

The present invention addresses the need to provide the orthopaedic surgeon with greater flexibility in the selection of implant components to suit the needs of an individual patient.

In one aspect, the present invention addresses the need for greater flexibility by providing a modular orthopaedic implant system comprising a first component and a tapered metaphyseal component. The first component has an articulating surface and an interior surface defining a tapered bore. The first component also has an exterior surface spaced from the articulating surface. At least a portion of the exterior surface surrounds the tapered bore. The portion of the exterior surface surrounding the tapered bore is asymmetrical in at least one cross-section. The tapered metaphyseal component is mountable to the distal femoral component.

In another aspect, the present invention provides an orthopaedic implant system comprising a first orthopaedic component and a metaphyseal component. The metaphyseal component is mountable to the first orthopaedic component. The metaphyseal component has a wide end, a narrow end, an overall length between the wide end and narrow end, and a tapered outer surface. The tapered outer surface of the metaphyseal component includes a plurality of steps and is porous over a majority of the overall length of the metaphyseal component.

In another aspect, the present invention provides an orthopaedic knee implant system comprising a distal femoral component and a metaphyseal component. The distal femoral component has an articulating surface and a non-articulating surface. The metaphyseal component is mountable to the non-articulating surface of the distal femoral component. The metaphyseal component has a wide end, a narrow end, an overall length between the wide end and narrow end, and a tapered outer surface. The tapered outer surface of the metaphyseal component includes at least five steps per inch of the overall length of the metaphyseal component.

In another aspect, the present invention provides an orthopaedic knee implant system comprising a distal femoral component and a metaphyseal component mountable to the first orthopaedic component. The distal femoral component has an articulating surface and a non-articulating surface. The metaphyseal component has a wide end, a narrow end, an overall length between the wide end and narrow end, and a tapered outer surface. The tapered outer surface of the metaphyseal component includes a plurality of adjacent steps extending from the wide end to the narrow end, each step being spaced from the adjacent step by a distance of less than 0.2 inches.

In another aspect, the present invention provides an orthopaedic implant system comprising a first implantable component and a second implantable component. The first implantable component has an articulating surface to replace a portion of a patient's bone. The first implantable component also has a tapered bore. The second implantable component has a tapered bore differing from the tapered bore of the first implantable component in at least one characteristic. The system further includes an adapter for connecting the first implantable component to the second implantable component. The adapter includes two tapered posts. One of the tapered posts is sized and shaped to be received in and frictionally lock with the tapered bore of the first implantable component. The other tapered post is sized and shaped to be received in and frictionally lock with the tapered bore of the second implantable component.

In another aspect, the present invention provides a modular orthopaedic knee implant system comprising a distal femoral component, a tapered metaphyseal component and two stem extensions. The distal femoral component has a distal articulating surface. The tapered metaphyseal component has a distal end and a proximal end with an opening at the proximal end. The tapered metaphyseal component is mountable to the distal femoral component. The first femoral stem extension has a distal end and a proximal end; the distal end is shaped and sized to be received in and mate with the opening at the proximal end of the tapered metaphyseal component. The second femoral stem extension also has a distal end and a proximal end; the distal end of the second femoral stem extension is different from the distal end of the first femoral shape in size or shape. The system further includes an adapter for connecting the second femoral stem extension to the tapered metaphyseal component. The adapter has a proximal end and a distal end. The adapter distal end is sized and shaped to be received in and mate with the opening at the proximal end of the tapered metaphyseal component. The adapter proximal end has an opening sized and shaped to receive and mate with the distal end of the second femoral stem extension.

In another aspect, the present invention provides an orthopaedic knee implant kit comprising a first distal femoral component, a second distal femoral component and a tapered metaphyseal component. The first distal femoral component has a distal articulating surface and a post. The second distal femoral component has a distal articulating surface and a proximal end with a bore at the proximal end. The tapered metaphyseal component has a proximal end and a distal end and has an interior surface defining a bore at the distal end. The bore of the tapered metaphyseal component is shaped and sized to receive a portion of the post of the first distal femoral component for mounting the tapered metaphyseal component on the first distal femoral component. The system also includes an adapter. The adapter has a distal end comprising a post shaped and sized to be received in the bore at the proximal end of the second femoral component. The adapter has a proximal end comprising a post shaped and sized to be received in the bore at the distal end of the tapered metaphyseal component. The tapered metaphyseal component may be selectively used with the first distal femoral component and the second distal femoral component.

BRIEF DESCRIPTION OF THE DRAWINGS

FIG. 9 is a perspective view of a femoral implant assembly illustrating a third style of distal femoral component assembled with the first style of femoral stem extension, the new universal modular metaphyseal sleeve component and a Morse taper post;

FIG. 10 is an exploded perspective view of the femoral implant assembly of FIG. 9;

FIG. 11 is a perspective view of a femoral implant assembly illustrating the third style of distal femoral component assembled with the second style of femoral stem extension, the new universal modular metaphyseal sleeve component, the Morse taper post and the second adapter;

FIG. 12 is an exploded perspective view of the femoral implant assembly of FIG. 11;

FIG. 37 is a side view of an embodiment of the first style of femoral stem extension of FIGS. 1-2, 5-6, 9-10 and 13-14, with part of the distal end shown in cross-section;

FIG. 38 is a side view of an alternative embodiment of the first style of femoral stem extension, with part of the distal end shown in cross-section;

FIG. 39 is a front view of an alternative embodiment of the first style of femoral stem extension, similar to the stem extension shown in FIG. 37 but of shorter length;

DETAILED DESCRIPTION

Figure 1:
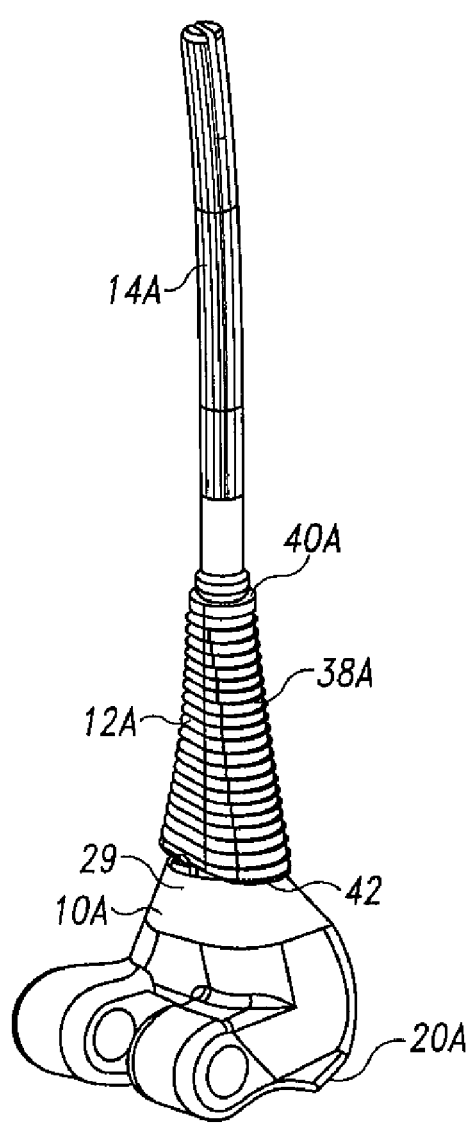
FIG. 1 is a perspective view of a femoral implant assembly illustrating a first style of distal femoral component assembled with a first style of femoral stem extension, a new universal modular metaphyseal sleeve component and a first adapter.
Figure 2:
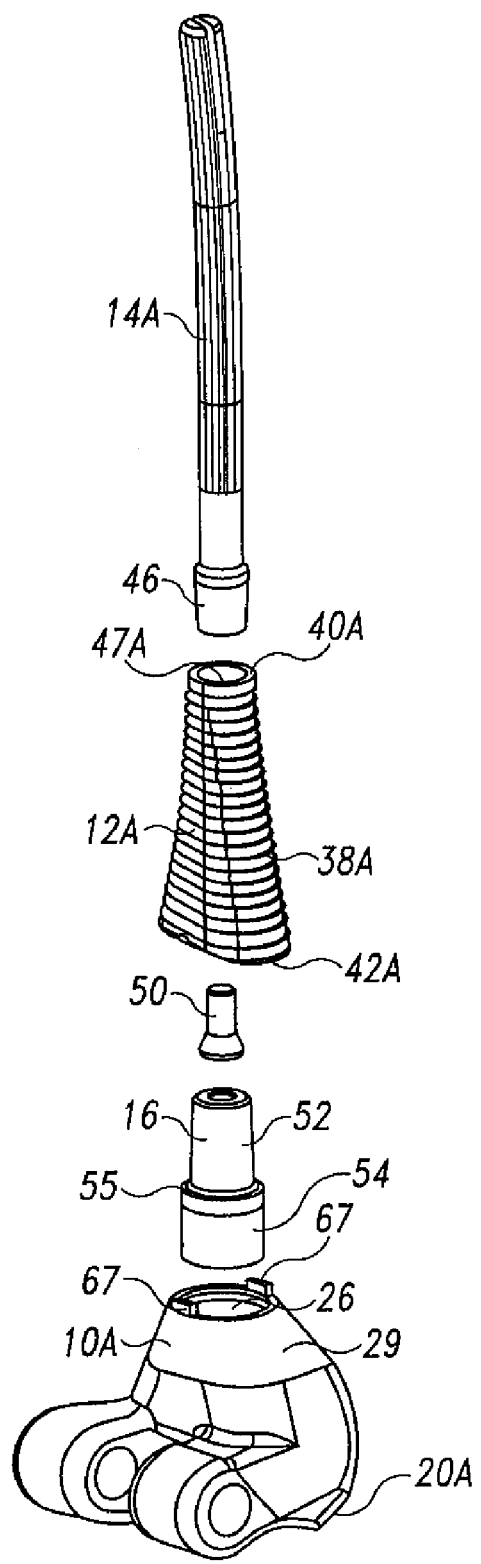
FIG. 2 is an exploded perspective view of the femoral implant assembly of FIG. 1.

A modular orthopaedic knee implant system incorporating the principles of the present invention is illustrated in the accompanying drawings. The illustrated modular orthopaedic knee implant system includes components of several existing orthopaedic knee implant systems, along with new components that provide the orthopaedic surgeon with greater flexibility in selecting the appropriate components to suit the needs of an individual patient. These patient needs can include factors such as individual anatomy and the condition of the native bone tissue.

FIGS. 1-16 illustrate various combinations of knee implant components that can be achieved utilizing the principles of the present invention. The combinations illustrated in FIGS. 1-16 include four different styles of distal femoral components 10A, 10B, 10C, 10D, a new universal modular metaphyseal sleeve component 12A and two different styles of femoral stem extensions 14A, 14B. The illustrated combinations can be made through the use of two adapters 16, 18. These femoral components 10A, 10B, 10C, 10D, stem extensions 14A, 14B and adapters 16, 18 can also be used with another embodiment of the new metaphyseal component 12B, shown in FIGS. 32-33 as well as with an existing metaphyseal component 12C, shown in FIGS. 34-35.

All of the illustrated distal femoral components 10A, 10B, 10C, and 10D are commercially available from DePuy Orthopaedics, Inc. of Warsaw, Ind. The first illustrated distal femoral component is part of the DePuy LPS System. This distal femoral component 10A is sized and shaped to replace the entire distal femur of a patient, as described more fully in U.S. patent application Ser. No. 10/135,791, entitled "Modular Limb Preservation System". The second illustrated distal femoral component 10B is a revision femoral component that is part of the DePuy LCS® Knee System. The third illustrated distal femoral component 10C is part of the DePuy P.F.C. SIGMA® Knee System. And the fourth illustrated distal femoral component 10D is part of the DePuy S-ROM Knee System. All of the illustrated distal femoral components 10A, 10B, 10C, 10D have a distal articulating surface 20A, 20B, 20C, 20D. For use in the present invention, all of these commercially available distal femoral components may have standard features for these systems. It should be understood that a typical surgical kit would be expected to have several sizes of each of the illustrated styles of distal femoral components.

It should be understood that although the principles of the present invention are described and illustrated with reference to implant components available from DePuy Orthopaedics, Inc., the invention is not limited to these components. The principles of the present invention can be applied to other implant components, including those of other manufacturers and those subsequently developed.

Some of the illustrated distal femoral components include parts that allow for use of a metaphyseal sleeve with the distal femoral component. For example, the illustrated distal femoral component 10B (LCS System) of FIGS. 5-8 has a Morse taper post 19. The illustrated Morse taper post 19 is sized and shaped to be received in and frictionally engage a Morse taper bore in a metaphyseal sleeve such as the existing metaphyseal sleeve 12C illustrated in FIGS. 34-35. The distal femoral component 10D of FIGS. 13-16 (S-ROM System) also has a Morse taper post 23 to be received in a distal Morse taper bore 21 of a metaphyseal sleeve such as the existing metaphyseal sleeve 12C of FIGS. 34-35. However, these two components 10B, 10D differ in several respects: for example, the distal femoral component 10D of the S-ROM System is designed to be connected to the tibial component (not shown) by means of a hinged connection while the distal femoral component 10B of the LCS System is not connected to the corresponding tibial component (not shown). The distal femoral component 10C of FIGS. 9-12 of the P.F.C. SIGMA System is also not connected to the corresponding tibial component (not shown). U.S. Pat. No. 6,171,342, U.S. Pat. No. 5,824,097 and U.S. Pat. No. 5,782,921, incorporated by reference herein in their entireties, disclose a Morse taper post such as that shown at 25 in FIGS. 10 and 12 that can be connected to a distal femoral component like that shown at 10C in FIGS. 9-12 with a threaded bolt such as that shown at 27 in FIGS. 10 and 12 so that the assembly can be used with an existing metaphyseal sleeve 12C.

Figure 36:
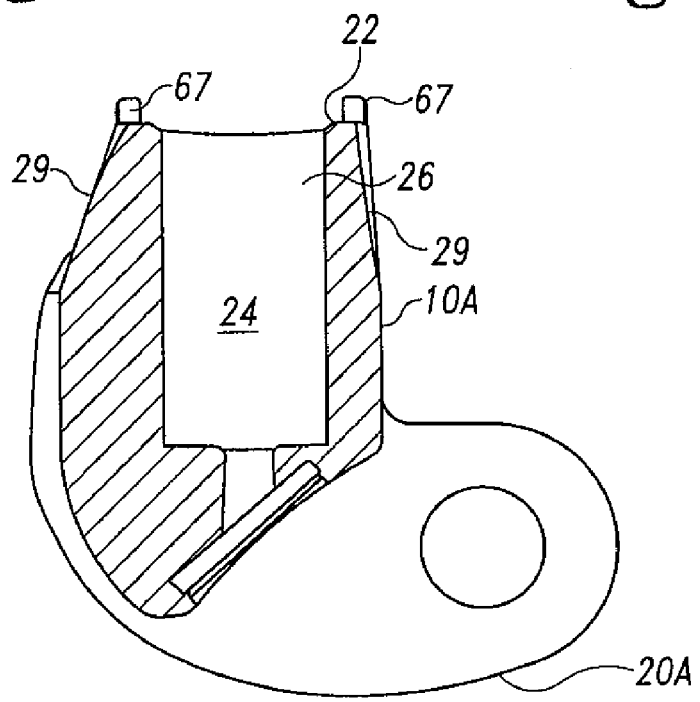
FIG. 36 is a cross-section of the first style of distal femoral component of FIGS. 1-4.

Referring to the first illustrated distal femoral component 10A, the distal femoral component 10A of FIGS. 1-4 of the LPS System is shaped to replace the entirety of the native femoral condyles. This distal femoral component 10A replaces more than 3-5 cm of the native distal femur. The first distal femoral component 10A has an interior surface 24 (see FIG. 36) defining a Morse taper bore 26 at its proximal end. As shown in FIG. 36, the portion of the exterior surface of the component 10A surrounding the bore 26 is not cylindrical, but diverges in the proximal direction; in addition, this portion of the exterior surface is asymmetrical in this cross-section. The Morse taper bore 26 is frustro-conical and widest at the proximal end, narrowing over its length. For example, the Morse taper bore 26 may have a diameter of 0.75 inches at its proximal end and a diameter of 0.715 inches nearer the distal end of the Morse taper bore 26, for example. The depth of the Morse taper bore 26 may be 1.39 inches for example. It should be understood that these and all dimensions provided in this description are provided for illustrative purposes only;

the invention is not limited to these dimensions or any other dimension unless expressly called for in one of the claims.

Figure 41:
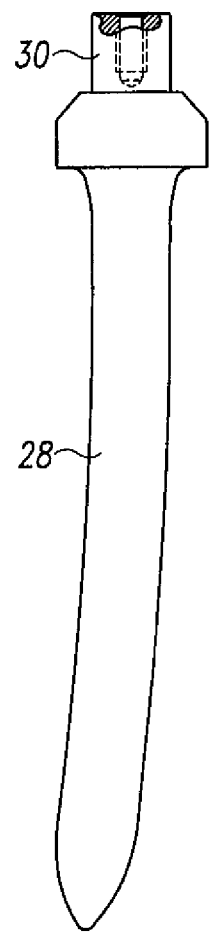
FIG. 41 is a side view of a stem component that can be used with the first style of distal femoral component of FIGS. 1-4 and 36.
Figure 42:
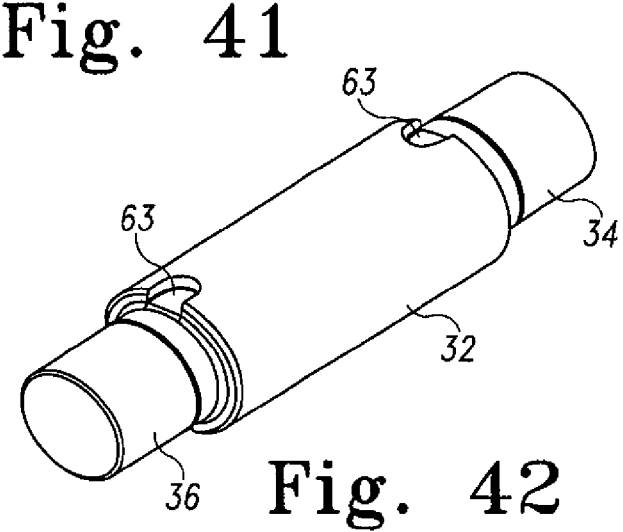
FIG. 42 is a perspective view of another component that can be used with the first style of distal femoral component of FIGS. 1-4 and 36.

The Morse taper bore 26 of the distal femoral component 10A of the LPS System is shaped to mate with a Morse taper post portion of other components provided as part of the LPS System. Other components of the LPS System that mate with the distal femoral component 10A are illustrated and described in U.S. patent application Ser. No. 10/135,791, entitled "Modular Limb Preservation System". Examples of such other components are illustrated in FIGS. 41 and 42: FIG. 41 illustrates a femoral stem extension 28 with a Morse taper post 30 that is sized and shaped to be received and lock in the Morse taper bore 26 of the distal femoral component 10A of the LPS System; FIG. 42 illustrates a segmental component 32 with two Morse taper posts 34, 36 that are sized and shaped to be received and lock in the Morse taper bore 26 of the distal femoral component 10A of the LPS System. The post-bore connections of the LPS System components are designed for a Morse taper fit so that the components are held together by friction when assembled.

In some patients, it may be desirable to use the LPS System as part of an end stage revision, where the native femoral condyles must be completely resected but where a portion of the metaphyseal flare of the native femur above the condyles can be spared. In such a situation, it would be desirable to use the standard distal femoral component 10A of the LPS System with a tapered metaphyseal component.

Figure 31:
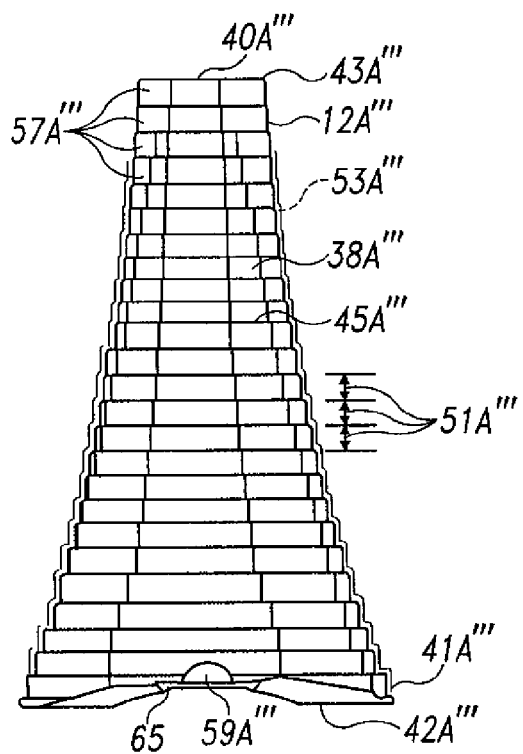
FIG. 31 is a front elevation of another size of the new universal modular metaphyseal sleeve component of FIGS. 1-16 and 23-28.
Figure 32:
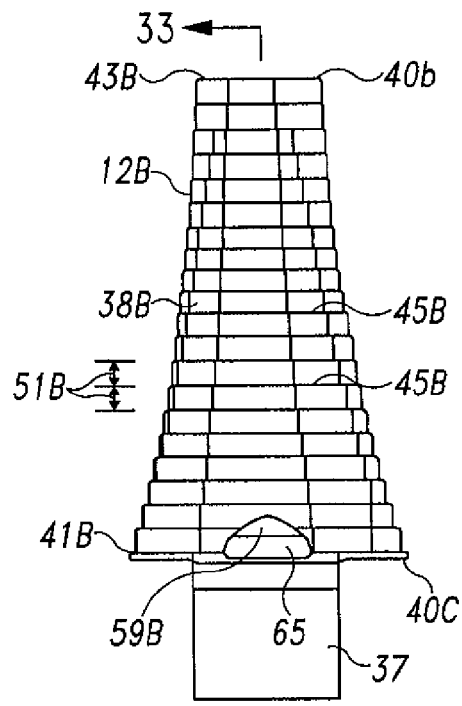
FIG. 32 is a side view of an alternative embodiment of a new metaphyseal component that can be used with the first style of distal femoral component of FIGS. 1-4 and 25.
Figure 33:
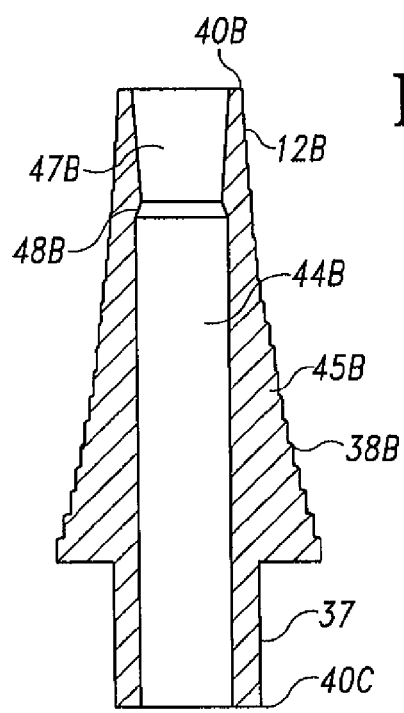
FIG. 33 is a cross-section of the new metaphyseal component of FIG. 33, taken along line 33-33 of FIG. 32.
Figure 34:
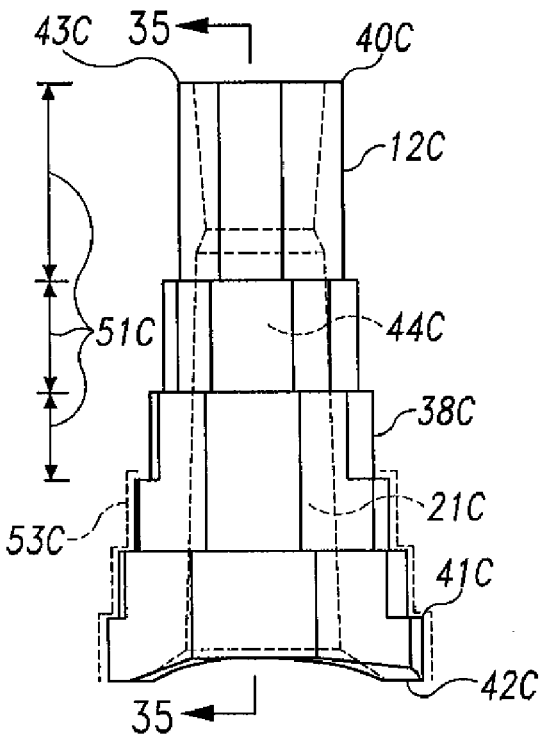
FIG. 34 is a front elevation of an existing metaphyseal sleeve component that can be used in the assemblies of FIGS. 1-16.
Figure 35:
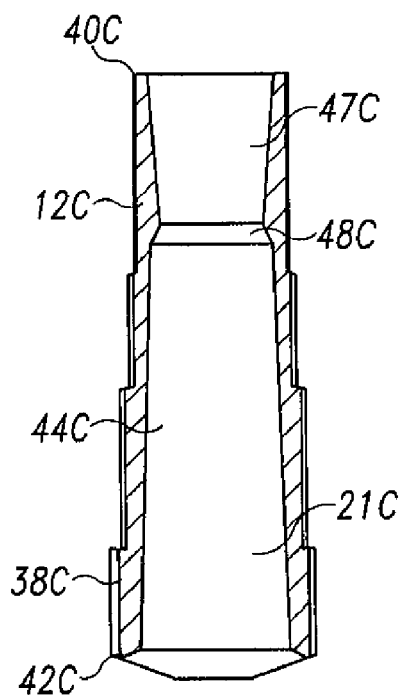
FIG. 35 is a cross-section of the existing metaphyseal sleeve component of FIG. 34, taken along line 35-35 of FIG. 34.

To meet this need for a metaphyseal component in combination with a distal femoral component 10A like that of the LPS System, a new metaphyseal component could be used, as illustrated in FIGS. 1-16 and 23-31 and described in more detail below. Another new metaphyseal component 12B that can be used with the distal femoral component 10A of the LPS System is illustrated in FIGS. 32-33. Alternatively, an existing metaphyseal component 12C of other implant systems, illustrated in FIGS. 34-35, could also be used with the first style of distal femoral component 10A. The existing metaphyseal component 12C of FIGS. 34-35 is part of DePuy Orthopaedics' S-ROM knee system.

Figure 23:
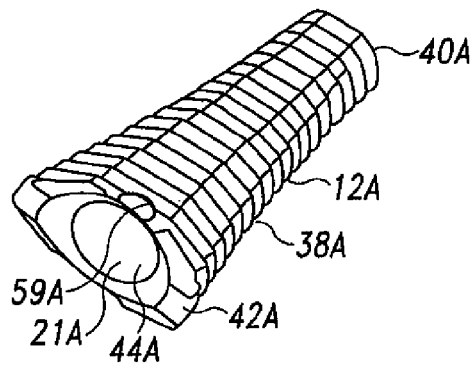
FIG. 23 is a perspective view of the new universal modular metaphyseal sleeve component of FIGS. 1-16.
Figure 24:
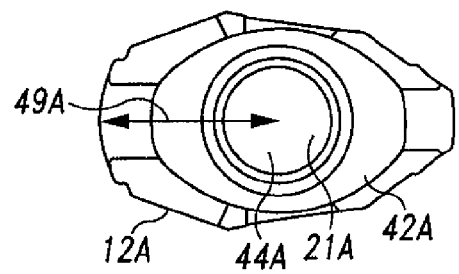
FIG. 24 is a distal end view of the new universal modular metaphyseal sleeve component of FIGS. 1-16 and 22.
Figure 25:
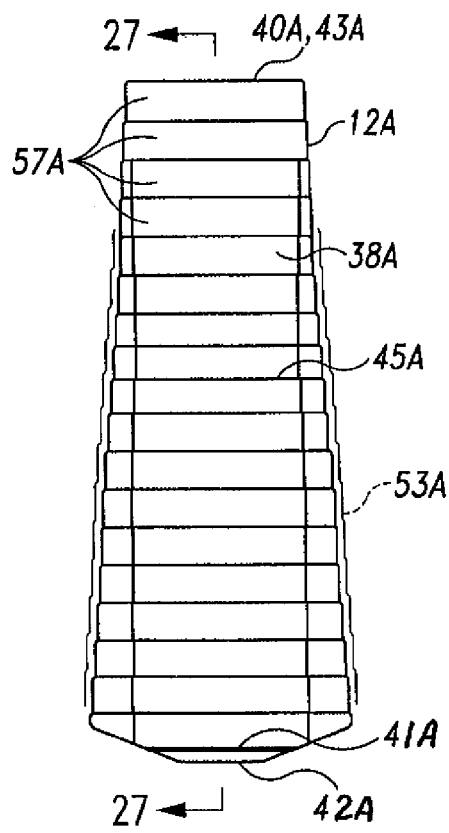
FIG. 25 is a side elevation of the new universal modular metaphyseal sleeve component of FIGS. 1-16 and 23-24.
Figure 28:
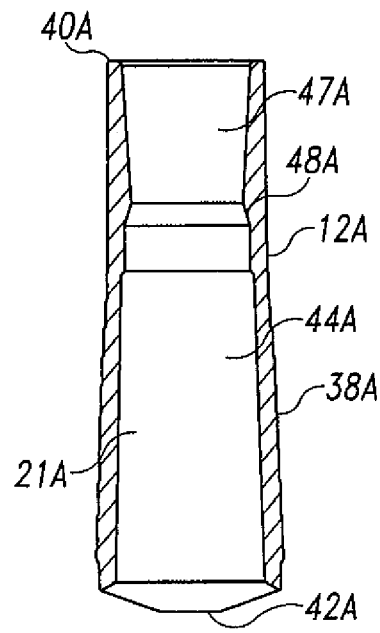
FIG. 28 is a cross-section of the new universal modular metaphyseal sleeve component of FIGS. 1-16 and 23-27, taken along line 28-28 of FIG. 26.
Figure 29:
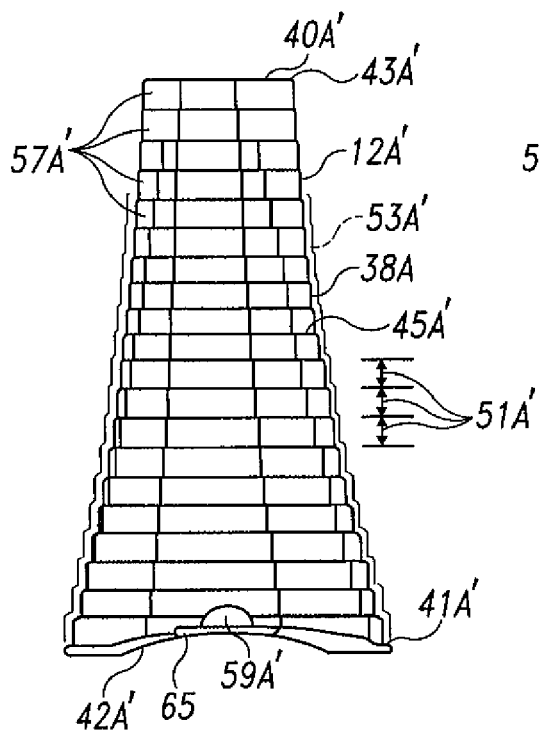
FIG. 29 is a front elevation of another size of the new universal modular metaphyseal sleeve component of FIGS. 1-16 and 23-28.
Figure 30:
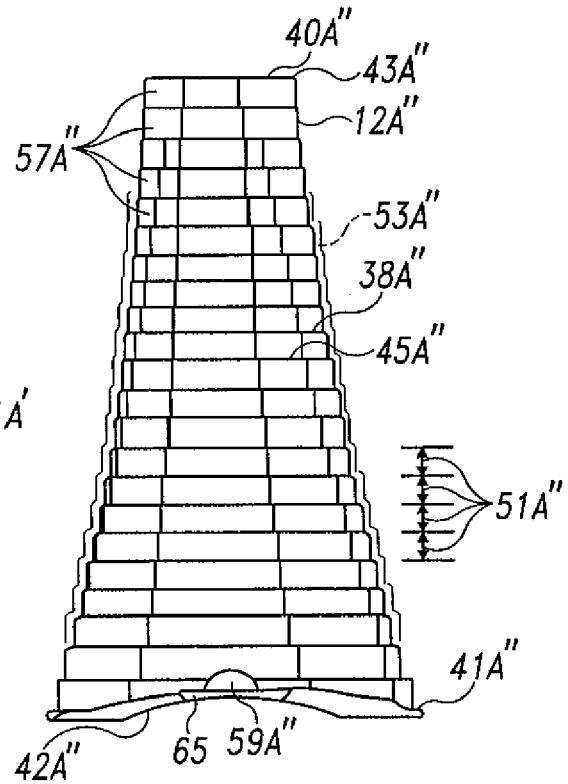
FIG. 30 is a front elevation of another size of the new universal modular metaphyseal sleeve component of FIGS. 1-16 and 23-28.

All of the illustrated metaphyseal components 12A, 12B, and 12C share some common features. As shown in FIGS. 23-25, each metaphyseal component 12A, 12B, 12C has a tapered outer surface 38A, 38B, 38C extending from a proximal end 40A, 40B, 40C to a distal end 42A, 42B, 42C. For each style of metaphyseal component 12A, 12B, 12C, several different sizes of metaphyseal components can be provided in a surgical kit. For the first illustrated style of metaphyseal component 12A, illustrated in FIGS. 1-16 and 23-31, four different sizes are shown: one size metaphyseal component 12A is illustrated in FIGS. 1-16 and 23-28; a second, longer (and wider in the medial-lateral direction) size metaphyseal component 12A' is illustrated in FIG. 29; a third, longer size metaphyseal component 12A" is illustrated in FIG. 30; and a fourth, longer size metaphyseal component 12A''' is illustrated in FIG. 31. It should be understood that a surgical kit could include fewer or more sizes of metaphyseal components. It should also be understood that although only a single size of metaphyseal component is shown for the components 12B and 12C of the styles of FIGS. 32-35, a surgical kit utilizing these styles of components would typically have a plurality of sizes of these components available for the surgeon.

All three illustrated styles of metaphyseal components 12A, 12B, and 12C have interior channels 44A, 44B, 44C. In the first new metaphyseal sleeve component 12A and the existing metaphyseal sleeve component 12C, the interior channel 44A, 44C tapers in the proximal direction from the distal end to define a distal Morse taper bore 21A, 21C. The bore 21C of the existing metaphyseal component 12C and bore 21A of the first new metaphyseal component 12A are both sized and shaped to be capable of fitting over and frictionally locking with the Morse taper post 23 of the distal femoral component 10D of the S-ROM System (see FIG. 14). Both the first and third styles of metaphyseal components 12A, 12C are also capable of fitting over and frictionally locking with the post 19 of the LCS System femoral component 10B and post 25 of the P.F.C. SIGMA System. As discussed below, in combination with the adapter 16, the first and third styles of metaphyseal components 12A, 12C are also capable of being used with the distal femoral component 10A of the LPS System.

The distal femoral component 10A of the LPS System can also be used with the second illustrated style of metaphyseal component 12B. In the second new metaphyseal component 12B, there is no distal Morse taper bore. Instead, the second style metaphyseal component 12B has a distal Morse taper post 37 (see FIGS. 32-33) sized and shaped like the Morse taper posts of other components of the LPS System, such as posts 30, 34 and 36 of the components 28, 32 illustrated in FIGS. 41-42, so that the distal Morse taper post 37 of the second style metaphyseal component 12B is capable of fitting into and frictionally locking with the Morse taper bore 26 (see FIG. 36) of the distal femoral component 10A of the LPS System.

The proximal ends of the interior channels 44A, 44B, 44C of all three styles of metaphyseal components 12A, 12B, 12C are similar. In all three styles, the proximal end of the interior channel tapers in the distal direction to define a Morse taper bore 47A, 47B, 47C that is sized and shaped to receive and frictionally lock with a Morse taper post 46 at the distal end of a first style of stem extension, shown at 14A in FIGS. 1-2, 5-6, 9-10, 13-14 and 37-39. The interior channel 44A, 44B, 44C of each style of metaphyseal component 12A, 12B, 12C also has an annular seat 48A, 48B, 48C (see FIGS. 27-28, 33 and 35) for a screw or bolt shown at 50 in FIGS. 2, 6 and 10.

Although all three illustrated styles of metaphyseal components 12A, 12B, 12C have stepped outer surfaces 38A, 38B, 38C, the configurations and surface finishes of the outer surfaces 38A, 38B new metaphyseal components 12A, 12B differ from the configuration and surface finish of the outer surface 38C of the existing metaphyseal component 12C. First, as can be seen from a comparison of FIGS. 23, 25, 26 and 29-33, the new metaphyseal components 12A, 12B have more steps than the existing metaphyseal component 12C. The smallest new metaphyseal component 12A of FIGS. 23-28 has a total of 19 tapering steps, from a distal step 41A to a proximal step 43A. The next larger size of the first metaphyseal component 12A' has a total of 21 steps from the distal step 41A' to the proximal step 43A' (see FIG. 29). The next larger size of the first metaphyseal component 12A" has a total of 23 steps from the distal step 41A" to the proximal step 43A" (see FIG. 30). And the largest size of the first metaphyseal component 12A''' has a total of 26 steps from the distal step 41A''' to the proximal step 43A''' (see FIG. 31). Illustrative intermediate steps are shown at 45A, 45A', 45A" 45A''' and 45B in FIGS. 25-26 and 29-33. The different sizes of the second new metaphyseal component 12B would have similar numbers of steps. Similar step configurations can be used for the second new metaphyseal component 12B of FIGS. 32-33. It should be understood that the number of steps for the different sizes of new metaphyseal components 12A, 12B in the illustrated examples are provided as examples only; the present invention is not limited to any particular number of steps unless expressly set forth in the claims.

In the first and second illustrated styles of metaphyseal components 12A, 12B, each step gradually tapers from the largest step 41A, 41B at the distal end 42A, 42B to the smallest step 43A, 43B at the proximal end 40A, 40B. For example, referring to FIG. 24, the dimension shown at 49A increases by 0.008 inch between the most proximal step 43A and the adjacent step. The distance shown at 49A gradually increases with each step, and the change in the distance 49A also gradually increases with each step toward the distal step 41A. In the metaphyseal component 12A with 19 steps (FIGS. 23-28), the distance 49A increases by 0.30 inch between the step adjacent the distal step 41A and the distal step 41A. In the metaphyseal component 12A' with 21 steps, the distance 49A increases by 0.035 inch between the step adjacent the distal step 41A' and the distal step 41A'. In the metaphyseal component 12" with 23 steps, the distance 49A increases by 0.039 inch between the step adjacent the distal step and the distal step 41A". In the metaphyseal component 12A''' with 26 steps, the distance 49A increases by 0.039 inch between the step adjacent the distal step 41A''' and the distal step 41A'''. The distance between steps, shown at 51A, 51A', 51A", 51A''' and 51B in FIGS. 26 and 29-31, is generally about 0.120-0.160 inch in the illustrated embodiment. With overall lengths of 2.390, 2.660, 2.960 and 3.340 inches, the first illustrated style of new metaphyseal components 12A, 12A', 12A" and 12A''' have an average of about 7.5-8 steps/inch of overall length of the metaphyseal component 12A, 12A', 12A", 12A'''. It should be understood that these dimensions and ratios are provided as examples only; the present invention is not limited to any particular dimension or proportion of dimensions unless expressly called for in the claims.

In contrast to the new metaphyseal components 12A, 12B, the steps defining the outer surface 38C of the existing metaphyseal component 12C have a different configuration and fewer steps, both overall and per inch of overall length of the metaphyseal component 12C. In the existing metaphyseal component 12C, the dimension corresponding with the dimension shown at 49A increases by 0.19-0.28 inch between the most distal step 41C and the adjacent step. The distance shown at 49C gradually increases by about 0.59-0.60 inch with each step. The distance between steps, shown at 51C in FIG. 34, ranges from about 0.19 inches to 0.83 inches, and the ratio of number of steps to overall length ranges from about 2.45 to 3.15 steps/inch.

The above-described differences in the configurations of the steps of the outer surfaces of the new metaphyseal components 12A, 12B and the existing metaphyseal component 12C result in differences in the degree of contact between the outer surfaces 38A, 38B, 38C of the metaphyseal components 12A, 12B, 12C and native bone tissue when the metaphyseal components are implanted. The smaller, shallower steps of the new metaphyseal components 12A, 12B and the increased number of steps of the new metaphyseal components 12A, 12B should result in the outer surfaces 38A, 38B of the new metaphyseal components 12A, 12B more closely approximating the shape of the cavity created in the metaphyseal bone by the broach during distal femoral bone preparation. Any gap between the metaphyseal component 12A, 12B and the native bone should be decreased, resulting in more intimate contact between the outer surfaces 38A, 38B of the metaphyseal components 12A, 12B and the bone, and greater contact area between the outer surfaces 38A, 38B of the metaphyseal components 12A, 12B and the bone.

In addition to the above-described differences in configuration of the stepped outer surfaces, the new metaphyseal components 12A, 12B also differ from the existing metaphyseal component 12C in the finish of the stepped outer surfaces 38A, 38B, 38C. In the first new metaphyseal component 12A, the stepped outer surface 38A of the component 12A is porous for most of its length and smooth for a short portion at its proximal end. In the second new metaphyseal component 12B, the stepped outer surface 38B of the component 12B is porous along its entire length. In the existing metaphyseal component 12C, the stepped outer surface 38C is smooth for a majority of its length and porous near its distal end only.

As used herein, "porous" refers to a surface that is conducive to bone ingrowth for non-cemented fixation, and "smooth" refers to a surface that is not conducive to such bone ingrowth. Suitable porous surfaces can be made by many different methods: casting, embossing, etching, milling, machining, and coating such as by plasma-spraying or by bonding, for example. Bonded materials can comprise sintered metal beads, sintered metal mesh or screen, or sintered metal fibers, for example. Known, commercially available materials and techniques can be used to create the porous exterior surfaces of the metaphyseal components 12A, 12B: for example, POROCOAT® coating, available from DePuy Orthopaedics, Inc. of Warsaw, Ind., could be used, as well as other commercially available coatings. It should be understood that the above-identified examples of materials, methods and commercial products are provided as examples only; the present invention is not limited to any particular material, method or commercial product for the porous surfaces unless expressly called for in the claims. In addition, it should be understood that as additional materials and methods become available to create surfaces that promote bony ingrowth, it is believed that such other materials and methods may also be useful with the present invention.

Figure 26:
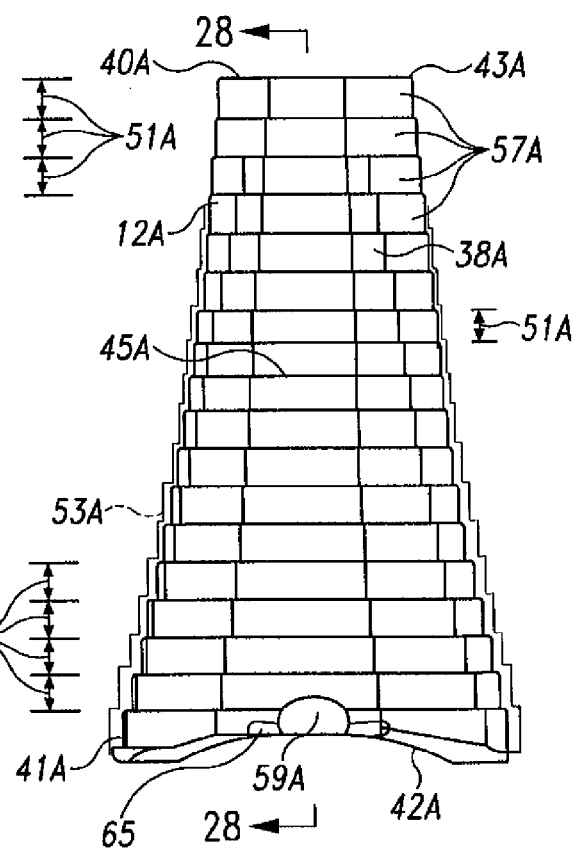
FIG. 26 is a front elevation of the new universal modular metaphyseal sleeve component of FIGS. 1-16 and 23-25.

In the first illustrated new metaphyseal component 12A, the outer surface 38A is porous from the distal end 42A to a level about 3 steps down from the most proximal step 43A so that about the top 0.554 inches (14 mm) is smooth rather than porous and the remainder of the outer surface 38A is porous. In FIGS. 25-26, the porous outer coating is illustrated by phantom lines 53A and the smooth portion of the outer surface is indicated at 57A. Generally, in the illustrated sizes of the first new metaphyseal 12A component, the outer surface 38A corresponding with at least about 75-80% of the overall height of the metaphyseal component 12A, 12A', 12A", 12A''' is porous. By providing a smooth outer surface at the proximal end of the metaphyseal component 12A, no bony ingrowth should occur at the proximal end. Since the proximal end of the metaphyseal component is the end that receives the distal end of the stem extension, it may be desirable to allow the proximal end of the metaphyseal component to flex somewhat so that stress is not unduly concentrated on the distal end of the stem extension. For this purpose, it is expected that a smooth surface from the proximal end to a point about 10-20 mm from the proximal end should suffice. However, it should be understood that the present invention is not limited to these dimensions or ratios unless expressly set forth in the claims. For example, the entire stepped outer surface 38B could be porous, as in the second illustrated new metaphyseal component 12B.

In contrast to the new metaphyseal components 12A, 12B, the existing metaphyseal component is generally porous along only a portion of the distal end. As illustrated in FIG. 34, the porous coating 53C (shown in phantom) extends up to the level of about the third step from the distal end 42C, leaving the remainder of the stepped outer surface 38C smooth.

Generally, of the three illustrated patterns of surface finishes, it is expected that in the months and years following implantation, there would be less bony ingrowth around the existing metaphyseal component 12C, so that the existing metaphyseal component 12C could be more easily removed if a later revision is required. Additional bony ingrowth may be more desirable in situations like end stage revision surgery, for example. Moreover, the benefits of increased bony ingrowth may outweigh any potential difficulty in removal.

The new metaphyseal components 12A, 12B may have additional features. As shown in FIGS. 23, 26 and 29-32, there may be notches 59A, 59B near the distal end of the metaphyseal sleeve 12A, 12B. These notches may be similar to those provided in the LPS System, as described in more detail in "Modular Limb Preservation System", referred to above, and shown at 63 in FIG. 42. With these notches 59A, 59B, the metaphyseal components 12A, 12B can be separated from an interlocking component using the tool described in U.S. patent application Ser. No. 10/229,203, entitled "Device, System and Method for Separation of Modular Orthopaedic Elements," filed on Aug. 27, 2002 by Hazebrouck, which is incorporated by reference herein in its entirety. The metaphyseal components 12A, 12B may also have distal grooves as shown at 65 in FIG. 24. These distal grooves 65 allow for version control when the new metaphyseal components are used with the first distal femoral component 10A. The grooves 65 allow the metaphyseal component 12A, 12B to be rotated when mounted on the distal femoral component 10A; otherwise rotation would be restricted by the tabs 67 of the distal femoral component 10A. The existing metaphyseal component 12C could be modified to include these features.

Figure 17:
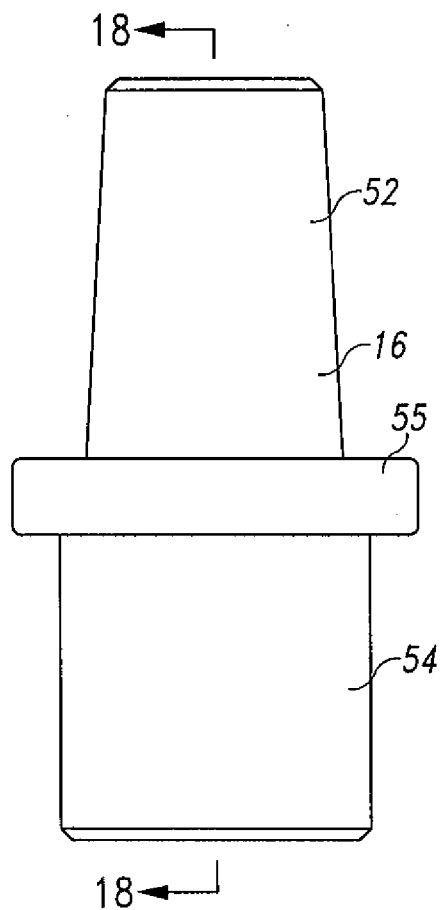
FIG. 17 is a side elevation of the first adapter of FIGS. 1-4.
Figure 18:
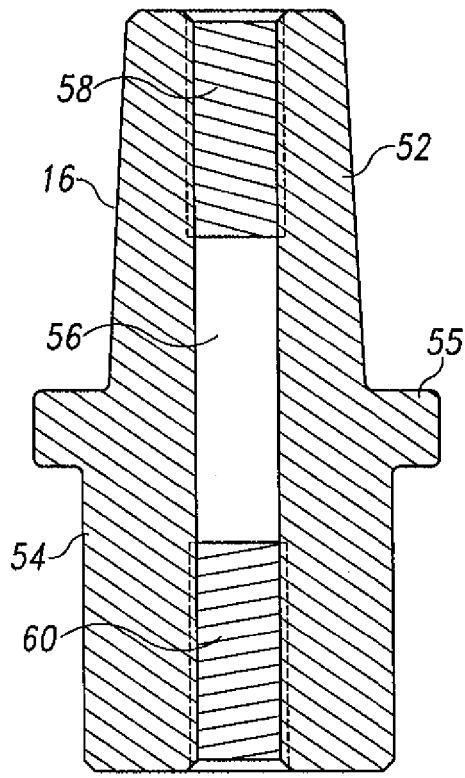
FIG. 18 is a cross-section of the first adapter, taken along line 18-18 of FIG. 17.
Figure 19:
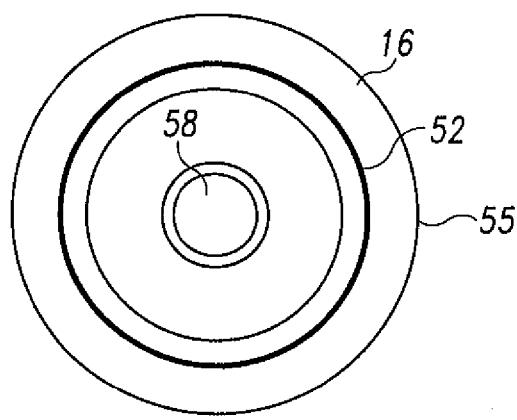
FIG. 19 is an end view of the adapter of FIGS. 17-18.

To allow the new metaphyseal component 12A and the existing metaphyseal component 12C to be used with the distal femoral component 10A of the LPS System, the system of the present invention includes an adapter 16. As shown in FIGS. 17-19, the illustrated adapter 16 has a proximal portion 52, a distal portion 54 and an annular collar 55 between the proximal portion 52 and distal portion 54.

The distal portion of the adapter 16 has an outer surface that is sized and shaped to be received within and frictionally lock with the Morse taper bore 26 of the LPS distal femoral component 10A. In other words, the outer surface of the distal portion defines a distal Morse taper post 54 that is sized and shaped like the Morse taper posts 30, 34, 36 of the other LPS components 28, 32 that are capable of being received in and mating with the Morse taper bore 26 of the distal femoral component 10A of the LPS System.

The annular collar 55 of the adapter 16 has an enlarged diameter to seat on a portion of the distal femoral component 10A of the LPS System to limit movement of the adapter in a distal direction.

The proximal portion of the adapter 16 has an outer surface that is sized and shaped to be received within and frictionally lock within the distal Morse taper bore 21A portion of the new metaphyseal component 12A and the distal Morse taper bore 21C of the existing metaphyseal component 12C. In other words, the proximal portion of the adapter 16 defines a proximal Morse taper post 52 that is sized and shaped to mimic the size and shape of the existing Morse taper posts of the S-ROM System, such as post 23 shown in FIGS. 14 and 16. This same shape of the existing Morse taper post 23 is also present in the post 19 of the distal femoral component 10B of the LCS revision System, illustrated in FIGS. 6 and 8. This same shape of the existing Morse taper post 23 may also be used for the post 25 to be assembled with the distal femoral component 10C of the P.F.C. SIGMA System.

As can be seen from FIGS. 1-4 and 17-18, the distal Morse taper post portion 54 of the adapter 16 is larger in diameter and shorter than the proximal Morse taper post portion 52 of the adapter 16. With these differently shaped and sized Morse taper post portions 52, 54, the adapter 16 can be used to connect components that lack commonly shaped and sized Morse taper bores, such as the distal femoral component 10A of the LPS System and the existing metaphyseal component 12C of the S-ROM System.

The illustrated adapter 16 has an interior channel 56 extending from its proximal end to its distal end. As shown in FIG. 18, the end parts 58, 60 of the interior channel 56 may be threaded to allow for screws or bolts to also be used for impaction or distraction In addition, the interior channel 56 provides an air passage to release pressure as the adapter 16 is connected to other components.

Thus, the first adapter 16 allows the first illustrated distal femoral component 10A to be used with the new metaphyseal component 12A as well as with the existing metaphyseal component 12C. Moreover, these metaphyseal components 12A, 12C can be used without the adapter 16 with the distal femoral components 10B, 10C, 10D of FIGS. 5-16. Thus, with the adapter 16, the first new metaphyseal component 12A and the existing metaphyseal component 12C are universal, usable across four different knee implant systems.

Figure 27:
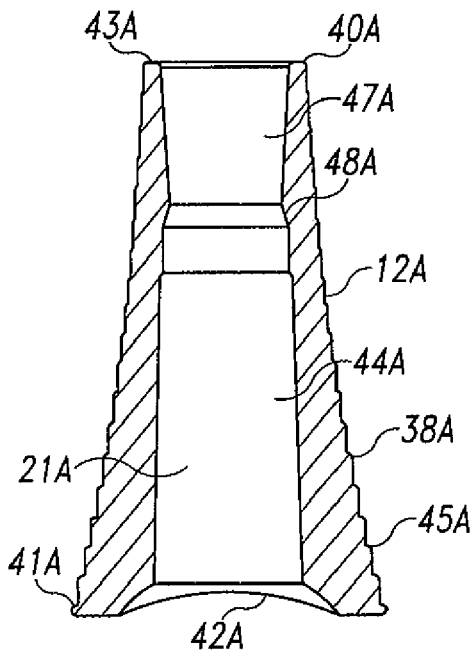
FIG. 27 is a cross-section of the new universal modular metaphyseal sleeve component of FIGS. 1-16 and 23-26, taken along line 27-27 of FIG. 25.

Since all three styles of metaphyseal components 12A, 12B, 12C have similar bores at their distal ends, all three metaphyseal components 12A, 12B, 12C can be used with femoral stem extensions 14A of DePuy Orthopaedics' S-ROM System. Examples of such femoral stem extensions 14A are illustrated in FIGS. 26-28. A surgical kit can include both straight and bowed femoral stem extensions, and stem extensions of various lengths and thicknesses. The femoral stem extensions provided in the kit may have outer surfaces designed for use in cemented or press fit applications; for example, the outer surfaces of the femoral stem extensions can have longitudinal grooves. In addition, the femoral stem extensions could have one or more slots such as shown in FIG. 37. All of these variations in the stem extension 14A features can be used with all three illustrated metaphyseal components 12A, 12B, 12C.

To provide the orthopaedic surgeon with even more choices in optimizing the knee implant assembly for the needs of the individual patient, the knee implant system of the present invention may be provided with a second adapter 18 to allow for use of all three metaphyseal components 12A, 12B, 12C with styles of stem extensions other than femoral stem extensions 14A of DePuy Orthopaedics' S-ROM System.

As shown in FIGS. 3-4, 7-8, 11-12, and 15-16, by use of the second adapter 18, the first new metaphyseal component 12A can be used with stem extensions having a distal end that would not normally provide a connection with the proximal end of the metaphyseal component 12A. For example, the second adapter 18 may allow the first new metaphyseal component 12A to be used with femoral stem extensions having end connections designed for use with DePuy Orthopaedics' P.F.C. SIGMA Knee implant system. The adapter 18 may also be used with the second new metaphyseal component 12B and the existing metaphyseal component 12C so that all three metaphyseal components 12A, 12B, 12C can be used with stem extensions 14B.

Figure 20:
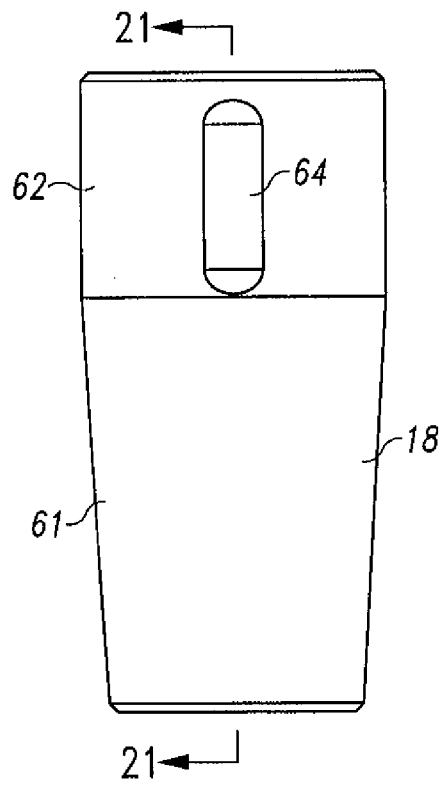
FIG. 20 is a side elevation of the second adapter of FIGS. 3-4, 7-8, 11-12 and 15-16.
Figure 21:
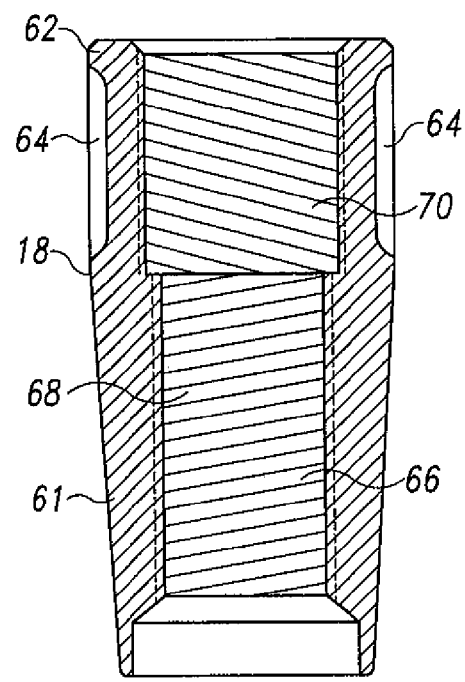
FIG. 21 is a cross-section of the second adapter, taken along line 21-21 of FIG. 20.
Figure 22:
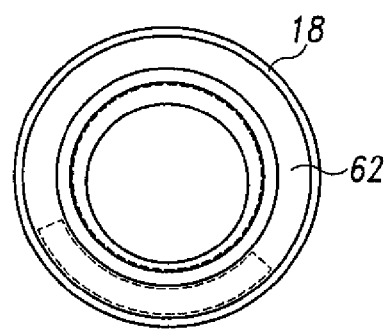
FIG. 22 is a proximal end view of the second adapter of FIGS. 20-21.

As shown in FIGS. 20-22, the second adapter 18 has an outer surface with a tapered distal portion and a proximal portion. The tapered distal portion defines a Morse taper post 61 that is sized and shaped to be received in and frictionally lock with the proximal Morse taper bore 47A, 47B, 47C of each metaphyseal component 12A, 12B, 12C. The proximal portion 62 of the outer surface of the second adapter 18 is substantially cylindrical in overall shape, with a plurality of indents 64 to allow the adapter 18 to be grasped by a tool such as a wrench (not shown).

Figure 40:
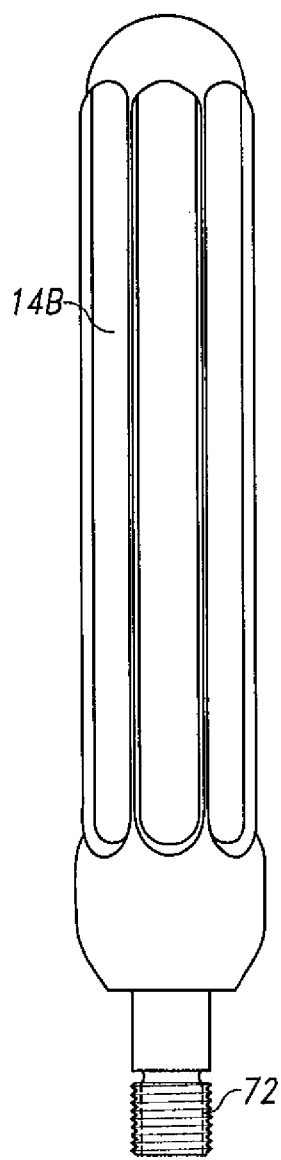
FIG. 40 is a side view of an embodiment of the second style of femoral stem extension.

As shown in FIG. 21, the second adapter 18 also has an interior channel 66. The distal portion 68 of the interior channel 66 is threaded to receive the threaded portion of the screw or bolt 50 for securing the second adapter 18 to the metaphyseal component 12A, 12B, 12C. The proximal portion 70 of the interior channel 66 is also threaded to receive the threaded distal end 72 of a stem extension 14B of the style shown in FIG. 40. As shown in FIG. 40, the threaded distal ends 72 of the existing stem extensions of the P.F.C. SIGMA System have reduced outer diameters and threaded outer surfaces.

The second style of stem extensions 14B may have standard features of the commercially available stem extensions of the P.F.C. SIGMA System. For example, these stem extensions 14B may be shaped for press fit or cemented application, and could be fully or partially porous coated. Other standard variations in the outer surfaces of the stem extensions can also be made. A typical surgical kit would include several sizes of such stem extensions 14B.

Thus, the present invention allows for use of any of the illustrated metaphyseal components 12A, 12B, 12C with the distal femoral component 10A of the LPS System, and allows two of the illustrated metaphyseal components 12A, 12C to be used with the other illustrated types of distal femoral components 10B, 10C, 10D. The present invention also allows all of the illustrated metaphyseal components 12A, 12B, 12C to be used with the revision distal femoral component 10B of the LCS System, the distal femoral component 10C of the P.F.C. SIGMA System, and the distal femoral component 10D of the S-ROM System. In addition, the present invention allows all three illustrated metaphyseal components 12A, 12B, 12C to be used not only with the standard femoral stem extensions 14A of the S-ROM System, but also with the commercially available stem extensions 14B of the P.F.C. SIGMA System. This increased flexibility is available without changing the existing connection mechanisms or the shapes and sizes in these existing knee systems.

For all of the Morse taper posts 19, 23, 25, 46, 52, 54, 61 and Morse taper bores 21A, 21C, 26, 47A, 47B, 47C described above, the length of the post would be less than or equal to the depth of the mating bore. The Morse taper posts 19, 23, 25, 46, 52, 54, 61 and bores 21A, 21C, 26, 27, 47A, 47B, 47C can be conically or frustoconically shaped. The angle of the frustoconical taper would be expected to be less than about 8°, and typically in the range of about 2-4°. Unless expressly called for in the claims, no particular angle or dimension is required for Morse taper posts 19, 23, 25, 46, 42, 54, 61 and bores 21A, 21C, 26, 27, 47A, 47B, 47C of the implant system of the present invention. Although the illustrated examples utilize Morse taper posts and bores, it should be understood that the present invention can be used with any style of interlocking posts and bores.

All of the components of the illustrated knee implant systems can be made of standard materials for such implants, such as titanium and cobalt-chrome.

In use, depending on the condition of the native bone tissue, the orthopaedic surgeon will determine the amount of bone to be resected from the femur and will select the most appropriate style of distal femoral component 10A, 10B, 10C, 10D for the individual patient and the most appropriate size of that style of component. Commercially available instrumentation can be used to resect the bone in the appropriate manner for the selected distal femoral component. If it is desirable to use a metaphyseal component to secure the implant in place, the surgeon can then select an appropriate size of metaphyseal component from the surgical kit and can prepare the bone to receive the metaphyseal component 12 using existing instrumentation. If the surgical kit includes metaphyseal components of the types shown as 12A and 12C in the drawings, the surgeon can also select the desired outer surface configuration and finish that best suits the needs of the individual patient. The surgeon can then select the most appropriate femoral stem extension 14A, 14B for the needs of the individual patient. The patient's intramedullary canal can be prepared to receive the femoral stem extension 14A, 14B in a conventional manner using existing surgical instrumentation.

If the most appropriate stem extension for the individual patient's needs is one having a distal end like those illustrated in FIGS. 1-2, 5-6, 9-10, 13-14, and 26-28, the surgeon can assemble the stem extension 14A and metaphyseal component 12A, 12B or 12C in a conventional manner, inserting the distal Morse taper post 46 of the stem extension 14A into the proximal Morse taper bore 47 of the metaphyseal component 12 and moving the two components 12, 14A into frictional engagement. The screw or bolt 50 can then be inserted through the metaphyseal component 12 and threaded into engagement with the internal threads 96 at the distal end of the stem extension 14A in a conventional manner.

If the most appropriate stem extension for the individual patient's needs is one having a distal end like those illustrated in FIGS. 3-4, 7-8, 11-12, 15-16 and 40, the surgeon can assemble the stem extension 14B and metaphyseal component 12A, 12B or 12C using the second adapter 18. To assemble the stem extension 14B, adapter 18 and metaphyseal component 12A, 12B or 12C, the surgeon would place the distal Morse taper post 61 of the second adapter 18 in the proximal Morse taper bore 47A, 47B or 47C of the metaphyseal component 12A, 12B or 12C, and move the two components into frictional engagement. Air pressure is released through the interior channel 66 of the second adapter 18 as the components 12, 18 are assembled. The screw or bolt 50 can be inserted through the distal bore of the metaphyseal component 12 and threaded onto the threaded internal bore 68 at the distal end of the second adapter 18 to secure these components together. The distal threaded end 72 of the stem extension 14B can then be inserted into the proximal threaded bore 70 of the adapter 18 and threaded onto the internal threads of the adapter 18. The subassembly of the metaphyseal component 12A, 12B or 12C, adapter 18 and the stem extension 14B is then ready for assembly with the distal femoral component.

Figures 7, 8:
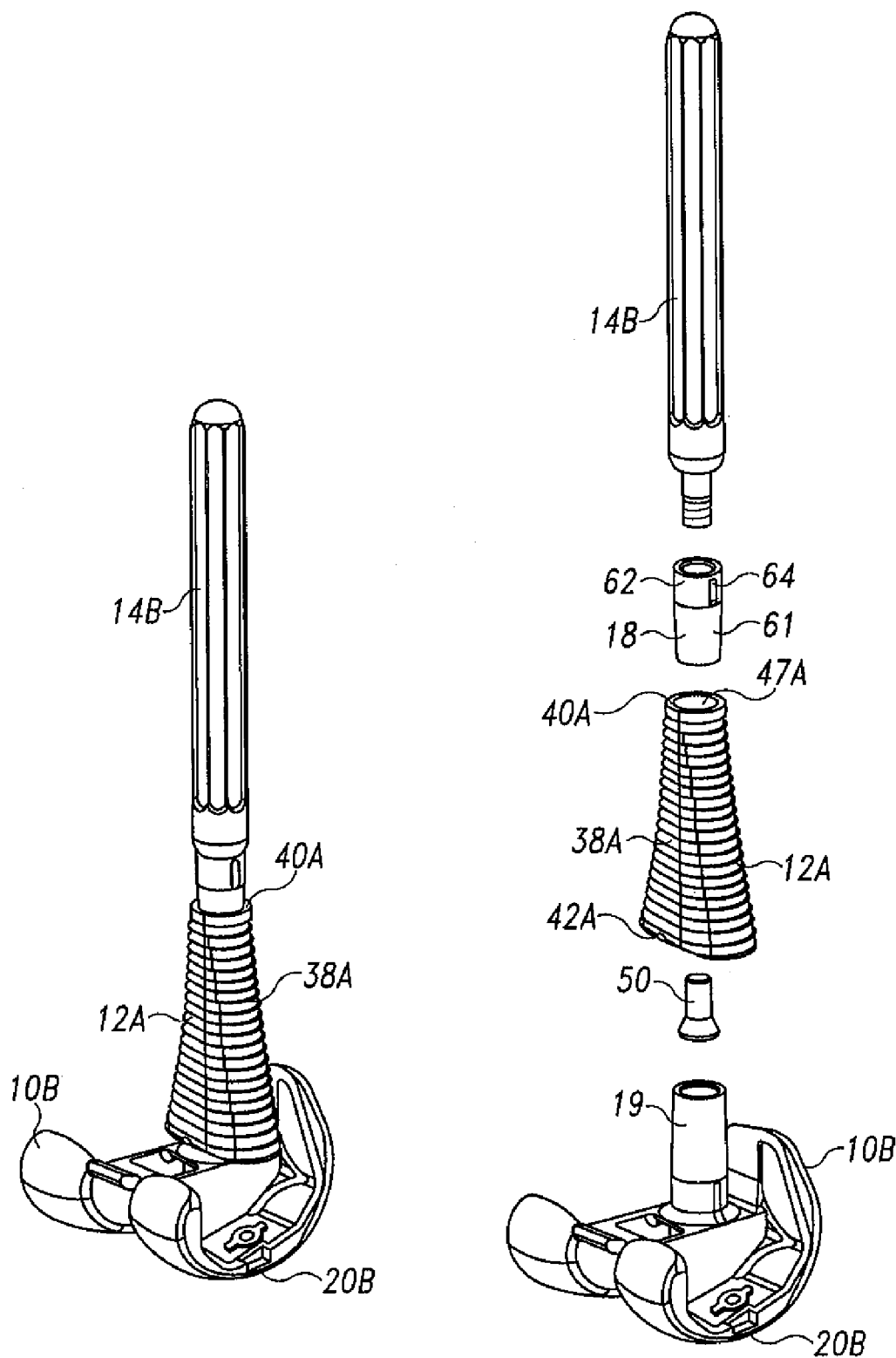
FIG. 7 is a perspective view of a femoral implant assembly illustrating the second style of distal femoral component assembled with a second style of femoral stem extension, the new universal modular metaphyseal sleeve component and the second adapter.
FIG. 8 is an exploded perspective view of the femoral implant assembly of FIG. 7.
Figure 13:
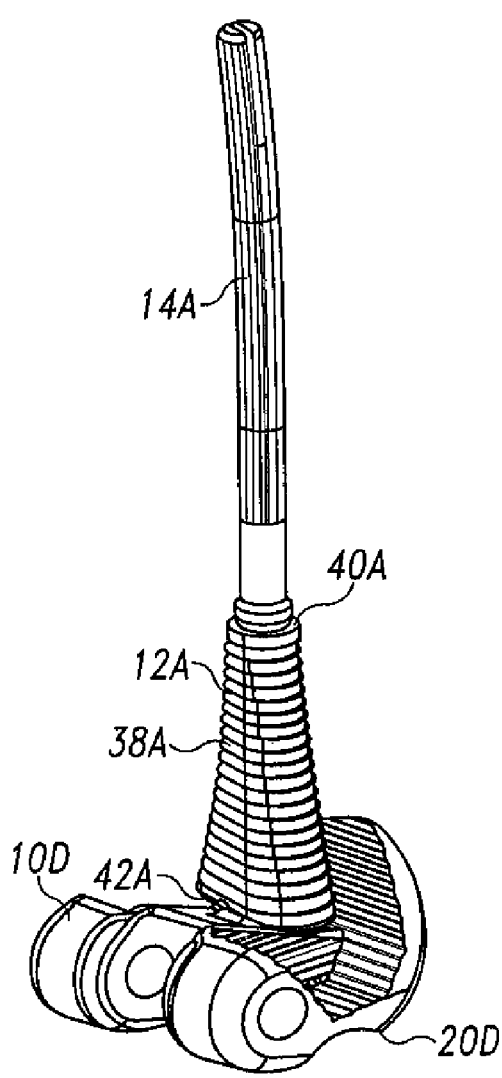
FIG. 13 is a perspective view of a femoral implant assembly illustrating a fourth style of distal femoral component assembled with the first style of femoral stem extension and the new universal modular metaphyseal sleeve component.
Figure 14:
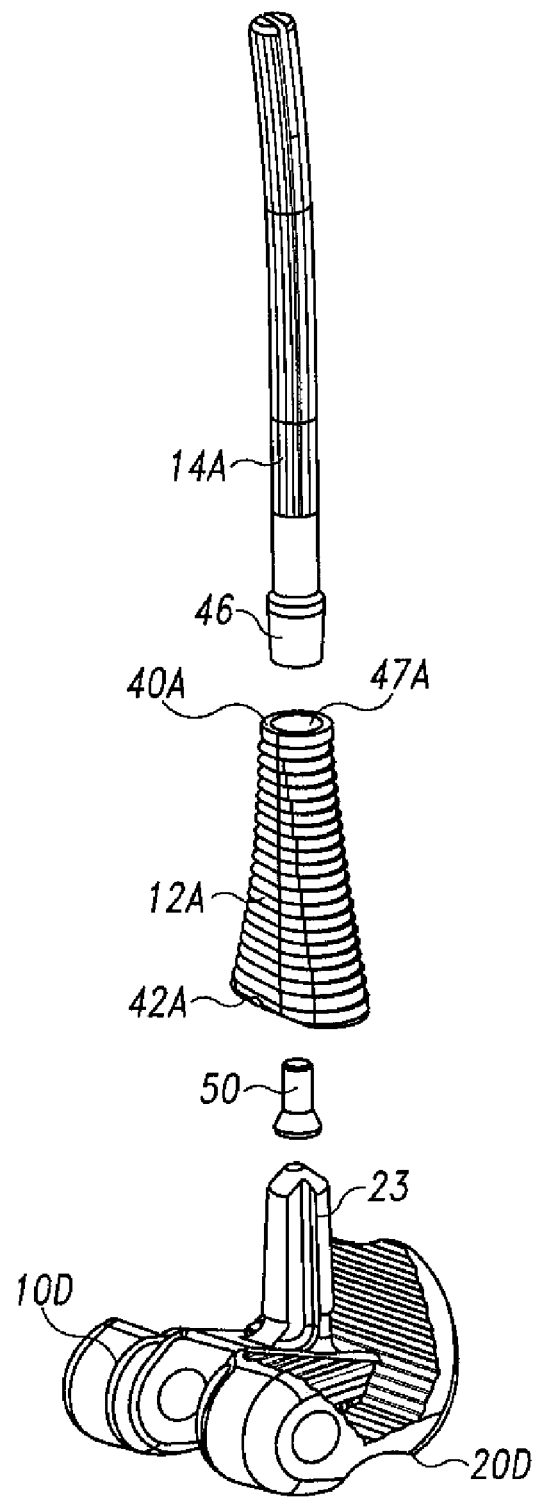
FIG. 14 is an exploded perspective view of the femoral implant assembly of FIG. 13.
Figures 15, 16:
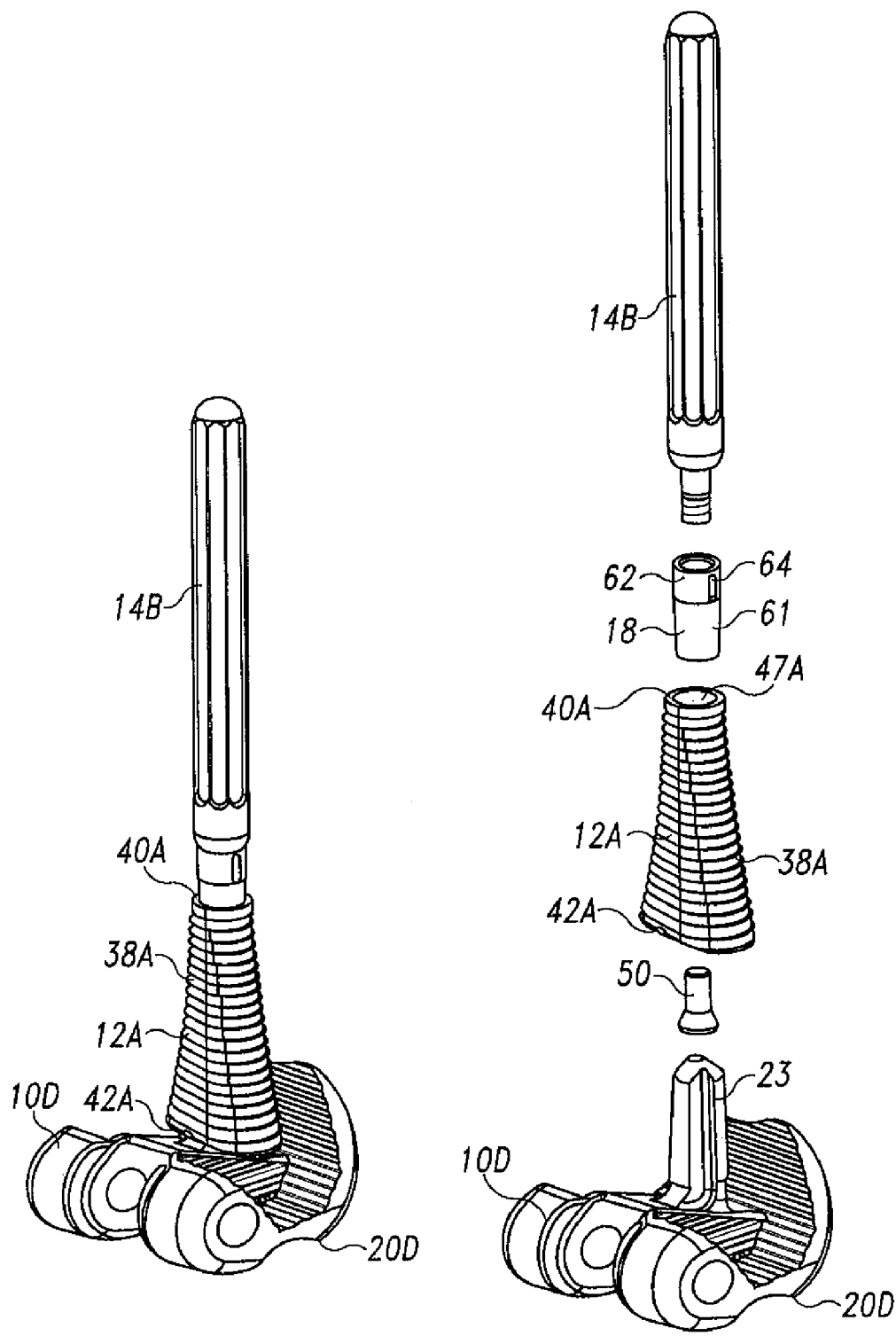
FIG. 15 is a perspective view of a femoral implant assembly illustrating the fourth style of distal femoral component assembled with the second style of femoral stem extension, the new universal modular metaphyseal sleeve component and the second adapter.
FIG. 16 is an exploded perspective view of the femoral implant assembly of FIG. 15.

If the most appropriate style of distal femoral component is that shown in FIGS. 5-8 and 13-16 as 10B or 10D, the metaphyseal component/stem extension subassembly or metaphyseal component/stem extension/second adapter subassembly can then be mounted on the existing stem or post 19, 23 of the distal femoral component 10B, 10D by inserting the stem or post 19, 23 into the distal Morse taper bore 21A or 21C (see FIGS. 27-28 and 35) of the metaphyseal component 12A or 12C and moving the components into frictional engagement. The complete assembly, as shown in FIGS. 7 and 13, can then be implanted.

Figures 3, 4:
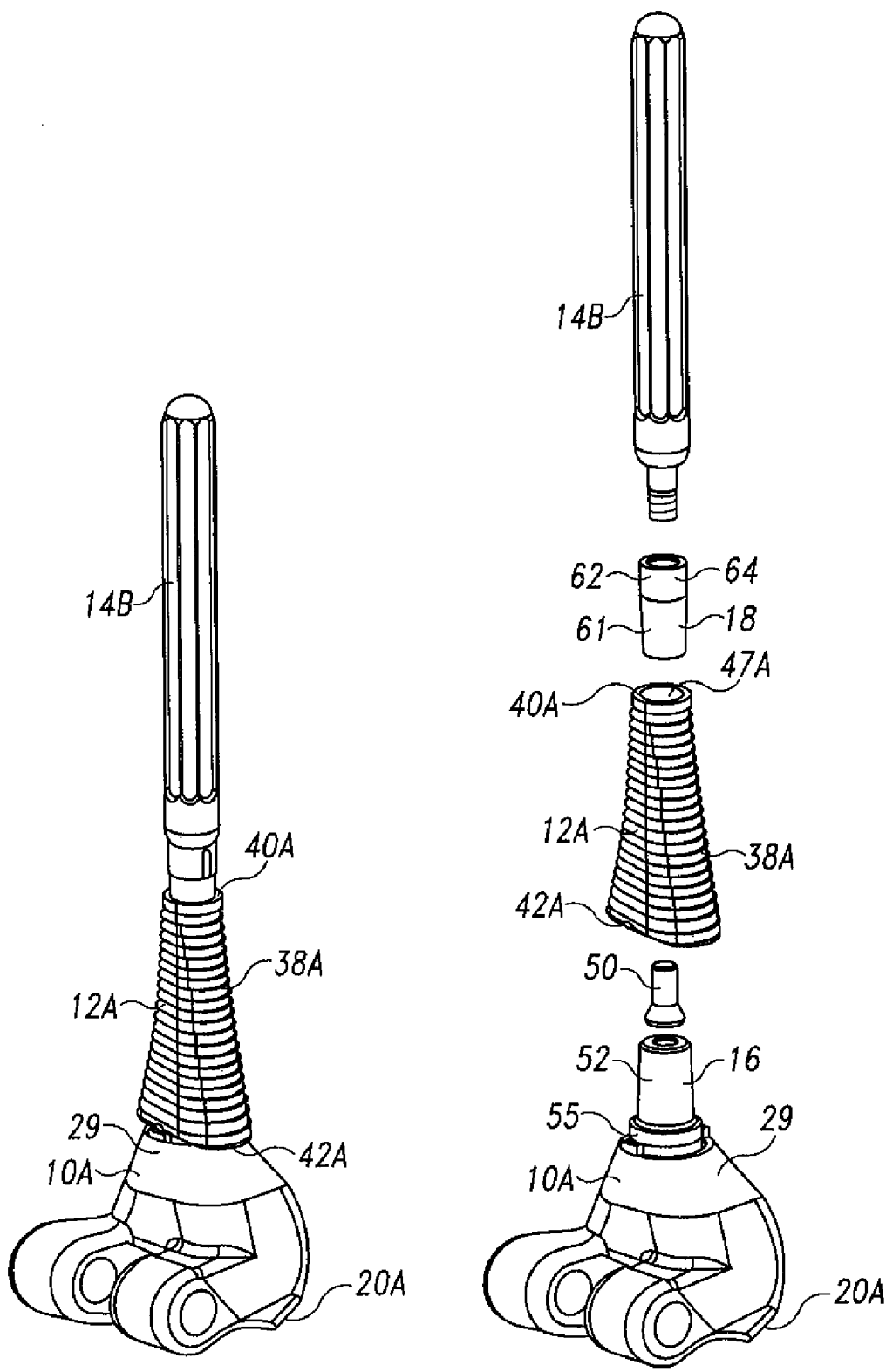
FIG. 3 is a perspective view of a femoral implant assembly illustrating the first style of distal femoral component assembled with a second style of femoral stem extension, the new universal modular metaphyseal sleeve component, a first adapter and a second adapter.
FIG. 4 is an exploded perspective view of the femoral implant assembly of FIG. 3.
Figure 5:
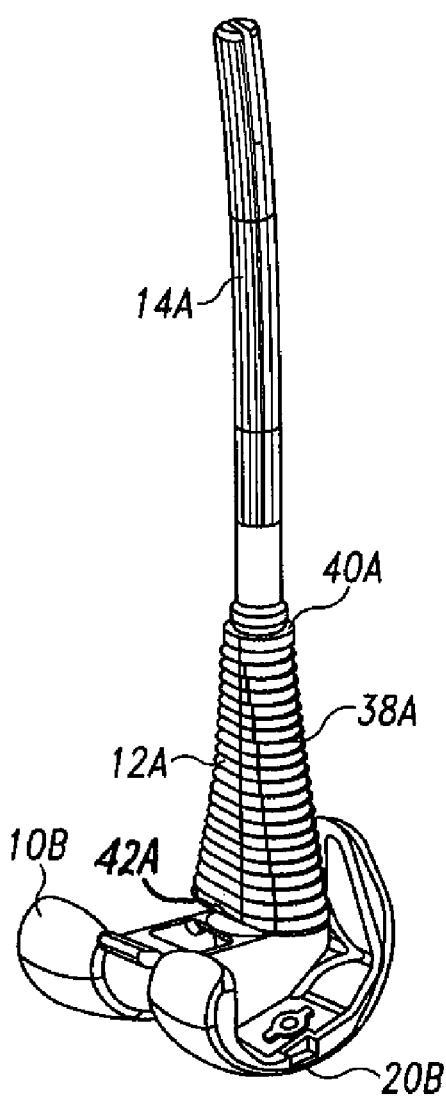
FIG. 5 is a perspective view of a femoral implant assembly illustrating a second style of distal femoral component assembled with the first style of femoral stem extension and the new universal modular metaphyseal sleeve component.
Figure 6:
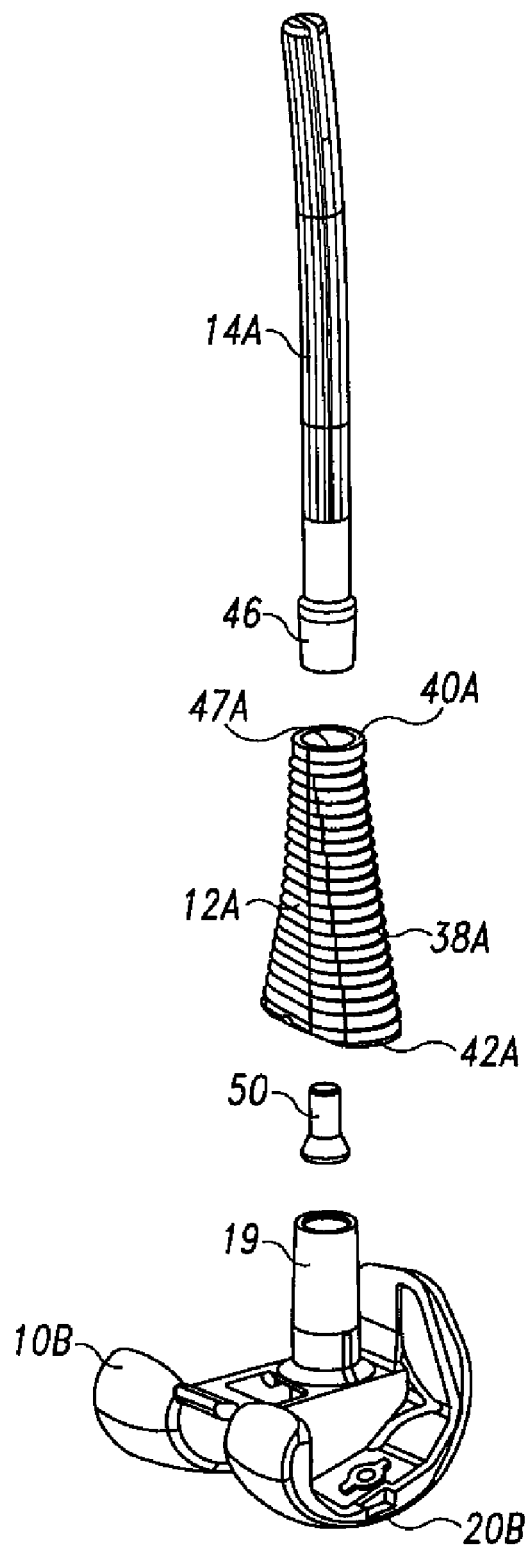
FIG. 6 is an exploded perspective view of the femoral implant assembly of FIG. 5.

If the most appropriate style of distal femoral component is that shown in FIGS. 1-4 and 25 as 10A, the surgeon would place the distal Morse taper post 54 of the adapter 16 into the Morse taper bore 26 of the distal femoral component 10A and move the two components 10A, 16 into frictional engagement. Air pressure is released through the interior channel of the adapter 16 as these components are assembled. The subassembly of the distal femoral component 10A and adapter 16 can then be assembled with the subassembly of the metaphyseal component 12A or 12C and the stem extension 14A, or subassembly of the metaphyseal component 12A or 12C, second adapter 18 and stem extension 14B. The two subassemblies can be moved together to frictionally engage the proximal Morse taper post 52 of the adapter 16 and the distal Morse taper bore 21A or 21C (see FIGS. 27-28 and 35) of the metaphyseal component 12A or 12C. The complete assembly, as shown in FIGS. 1 and 3, can then be implanted.

If the most appropriate style of distal femoral component is that shown in FIGS. 9-12 as 10C, the surgeon can assemble the femoral stem or post 25 to the distal femoral component 10C using the bolt 27 shown in FIGS. 10 and 12, and then insert the stem or bolt 50 into the distal Morse taper bore 21A or 21C (see FIGS. 27-28 and 35) of the metaphyseal component 12A or 12C of the subassembly. The post 25 and bore 21A or 21C can then be moved together into frictional engagement and the complete assembly as shown in FIGS. 9 and 11 can then be implanted.

If a metaphyseal component as shown in FIGS. 32-33 is used, the surgeon can first assemble the metaphyseal component 12b and the selected stem 14A, or metaphyseal component 12B, second adapter 18 and selected stem 14B into a subassembly. The subassembly can then be assembled with the distal femoral component 10A by inserting the distal Morse taper post 37 of the metaphyseal component 12B into the proximal Morse taper bore 26 of the distal femoral component 10A and then moving the components into frictional engagement. The assembled implant can then be implanted.

It should be understood that although not illustrated, the knee implant system or kit would also include tibial components that are designed to cooperate with the femoral implant assemblies. It should also be understood that some or all of the principles of the present invention could be applied to other implants, such as tibial implants.

It should also be understood that a typical surgical kit would also include trial implant components like those shown in FIGS. 1-16. The surgeon would typically assemble a trial implant and temporarily secure the trial implant assembly in place on the prepared bone to ensure that the assembled implant will be the optimum for the individual patient's needs. The trial components can have features like those described above for the final implant components.

In addition, a surgical kit utilizing the principles of the present invention could include several sizes of one style of metaphyseal component, such as the first new metaphyseal component 12A, the second new metaphyseal component 12B or the existing metaphyseal component 12C. Alternatively, such a surgical kit could include several sizes of two or more of the illustrated styles of metaphyseal components 12A, 12B, and 12C.

Various modifications and additions can be made to the above-described embodiment without departing from spirit of the invention. For example, the distal femoral component 10A could have a Morse taper bore 26 sized and shaped like the distal bore 21A or 21C of the metaphyseal component 12A or 12C. In such a case, the adapter 16 could be symmetrical about a central plane, so that the proximal and distal ends of the adapter could be used interchangeably. Moreover, the principles of the present invention could be applied to orthopaedic implants designed to replace joints other than the knees. Various other modifications and additions can be made, and all such modifications and additions are intended to fall within the scope of the claims unless the claims expressly call for a specific construction.

We claim:

1. A modular orthopaedic implant system comprising:
    a distal femoral component having a pair of spaced, curved distal articulating surfaces, a proximal end opposite the distal articulating surfaces, an interior surface defining a tapered bore at the proximal end, the tapered bore being widest at the proximal end and extending distally from the proximal end, and an exterior surface spaced from the distal articulating surfaces, at least a portion of the exterior surface surrounding the tapered bore, the portion of the exterior surface surrounding the tapered bore being asymmetrical in at least one cross-section, the maximum dimension of the distal femoral component in the proximal-distal direction being the distance from the distal articulating surfaces to the proximal end; and
    a tapered metaphyseal component mountable to the proximal end of the distal femoral component;
    wherein the tapered metaphyseal component has an outer surface including a plurality of steps, a proximal end and a distal end, the tapered metaphyseal component being widest at its distal end; and
    wherein the tapered metaphyseal component includes a tapered post sized and shaped to be receivable within the tapered bore of the distal femoral component and to create a frictional lock between the distal femoral component and the tapered metaphyseal component, the tapered post extending outwardly from the distal end of the tapered metaphyseal component and having a central longitudinal axis that extends through the proximal end of the metaphyseal component.

2. The modular orthopaedic implant system of claim 1 wherein the distal femoral component is sized and shaped to replace more than the distal 3 cm. of the native femur.

3. The modular orthopaedic implant system of claim 1 further comprising a plurality of orthopaedic components having tapered bores sized and shaped to be received in and frictionally lock with the tapered bore of the first component.

4. The modular orthopaedic implant system of claim 3 wherein at least one of the plurality of orthopaedic components comprises a segment sized and shaped to replace a portion of the shaft of a long bone.

5. The modular orthopaedic implant system of claim 1 wherein the tapered metaphyseal component has an interior surface defining an opening, the system further comprising:
    a first stem extension having a distal end and a proximal end, the distal end being shaped and sized to be received in and mate with the opening of the tapered metaphyseal component;
    a second stem extension having a distal end and a proximal end, the distal end of the second femoral stem extension being different from the distal end of the first femoral stem extension shape in size or shape;
    an adapter for connecting the second femoral stem extension to the tapered metaphyseal component, the adapter having an end sized and shaped to be received in and mate with the opening of the tapered metaphyseal component, and the adapter opposite end having an opening sized and shaped to receive and mate with the distal end of the second femoral stem extension.

6. The modular orthopaedic implant system of claim 5 wherein the distal end of the second stem extension is threaded.

7. A modular orthopaedic implant system comprising:
    a first component having a distal articulating surface, a proximal end opposite the distal articulating surface, an interior surface defining a tapered bore having an opening at the proximal end of the first component, the bore extending in a distal direction from the opening and being widest at the opening, and an exterior surface spaced from the articulating surface, at least a portion of the exterior surface surrounding the tapered bore, the portion of the exterior surface surrounding the tapered bore being asymmetrical in at least one cross-section, the maximum proximal-distal dimension of the first component being the distance from the distal articulating surface to the proximal end; and a tapered metaphyseal component mountable to the first component;

wherein the tapered metaphyseal component has an interior surface defining a distal tapered bore having a distal opening, the tapered bore being widest at the distal opening, the system further comprising an adapter for connecting the tapered metaphyseal component to the first component, the adapter having a longitudinal axis and a first tapered post sized and shaped to be receivable within the tapered bore of the first component and to create a frictional lock between the first component and the adapter, the adapter further comprising a second tapered post sized and shaped to be receivable within the distal tapered bore of the tapered metaphyseal component and to create a frictional lock between the adapter and the tapered metaphyseal component, wherein the first and second tapered posts of the adapter are aligned along the longitudinal axis of the adapter and are widest at a location between the ends of the adapter.

8. The modular orthopaedic implant system of claim 6 wherein the two tapered posts of the adapter are different from each other in size or shape, and wherein the two tapered posts are integral.

9. An orthopaedic implant system comprising:

a first implantable component comprising a distal femoral component having a pair of spaced curved distal articulating surfaces;

a second implantable component;

the first implantable component having a tapered bore;

the second implantable component having a tapered bore differing from the tapered bore of the first implantable component in at least one characteristic;

an adapter for connecting the first implantable component to the second implantable component, the adapter having a central longitudinal axis and including two uniformly tapered posts, one of said tapered posts defining one end of the adapter and being sized and shaped to be received in and frictionally lock with the tapered bore of the first implantable component and the other of said tapered posts defining the opposite end of the adapter and being sized and shaped to be received in and frictionally lock with the tapered bore of the second implantable component, the two posts being most narrow at the ends of the adapter, each post having a longitudinal axis, wherein the longitudinal axis of each post is collinear with the central longitudinal axis of the adapter.

10. The system of claim 9 wherein the second implantable component comprises a tapered metaphyseal component.

11. The system of claim 10 further comprising an implantable segment sized and shaped to replace a diaphyseal portion of a long bone, the implantable segment having a tapered post sized and shaped to be received in and frictionally lock with the tapered bore of the first implantable component.

* * * * *